(12) United States Patent
DiMauro et al.

(10) Patent No.: US 10,960,224 B2
(45) Date of Patent: Mar. 30, 2021

(54) TRANS-ORBITAL INFRARED LIGHT THERAPY

(71) Applicant: Janssen Pharmaceutica NV, Beerse (BE)

(72) Inventors: Thomas M DiMauro, Southboro, MA (US); Kevin Wildenhaus, Plymouth, MI (US); John Pracyk, Cumberland, RI (US); Michael Luedtke, Bellingham, MA (US)

(73) Assignee: Janssen Pharmaceutica NV, Beerse (BE)

( * ) Notice: Subject to any disclaimer, the term of this patent is extended or adjusted under 35 U.S.C. 154(b) by 52 days.

(21) Appl. No.: 15/839,954

(22) Filed: Dec. 13, 2017

(65) Prior Publication Data
US 2018/0193664 A1    Jul. 12, 2018

Related U.S. Application Data

(60) Provisional application No. 62/445,304, filed on Jan. 12, 2017.

(51) Int. Cl.
*A61N 5/06* (2006.01)

(52) U.S. Cl.
CPC .... *A61N 5/0622* (2013.01); *A61N 2005/0648* (2013.01); *A61N 2005/0651* (2013.01); *A61N 2005/0659* (2013.01); *A61N 2005/0662* (2013.01); *A61N 2005/0663* (2013.01)

(58) Field of Classification Search
CPC ...... A61N 5/06; A61N 5/0613; A61N 5/0622; A61N 2005/0632; A61N 2005/0635; A61N 2005/0643; A61N 2005/0648; A61N 2005/065; A61N 2005/0651; A61N 2005/062; A61N 2005/0653; A61N 2005/0659; A61N 2005/066; A61N 2005/0661; A61N 2005/0662; A61N 2005/0663

USPC ................ 607/88–91, 93, 108, 109; 128/898
See application file for complete search history.

(56) References Cited

U.S. PATENT DOCUMENTS

| 4,283,127 | A | 8/1981 | Rosenwinkle | |
|---|---|---|---|---|
| 6,350,275 | B1 | 2/2002 | Vreman | |
| 6,559,096 | B1 | 5/2003 | Smith | |
| 6,688,132 | B2 | 2/2004 | Smith | |
| 6,701,724 | B2 | 3/2004 | Smith | |
| 6,857,739 | B1 | 2/2005 | Watson | |
| 6,968,711 | B2 | 11/2005 | Smith | |
| 8,167,920 | B2 * | 5/2012 | DiMauro | A61B 17/688 128/898 |
| 8,734,498 | B2 * | 5/2014 | DiMauro | A61N 5/0603 128/898 |

(Continued)

OTHER PUBLICATIONS

Anders, "Light Supports Neurite Outgrowth of Human Neural Progenitor Cells In Vitro: The Role of P2Y Receptors", *IEEE J Quantum Electronics*, Jan./Feb. 2008, vol. 14 Issue 1, pp. 118-125.

(Continued)

*Primary Examiner* — Ahmed M Farah

(57) ABSTRACT

A device adapted to deliver red/NIR light through an eyelid of a patient, the device comprising:
  a) a nose bridge,
  b) a first orbital rim adapted to encircle a first eye, wherein the first orbital rim is attached to the bridge, and
  c) a red/NIR LED attached to the rim.

7 Claims, 24 Drawing Sheets

(56) References Cited

U.S. PATENT DOCUMENTS

| | | | |
|---|---|---|---|
| 9,470,908 B1 | 10/2016 | Frankel | |
| 10,561,857 B2* | 2/2020 | Toselli | A61N 5/0622 |
| 2001/0028431 A1 | 10/2001 | Rossin | |
| 2004/0215293 A1 | 10/2004 | Eels | |
| 2005/0278003 A1 | 12/2005 | Feldman | |
| 2006/0136018 A1 | 6/2006 | Lack et al. | |
| 2006/0198128 A1 | 9/2006 | Piepgras | |
| 2006/0259100 A1 | 11/2006 | Hilburg | |
| 2007/0195515 A1 | 8/2007 | Waters | |
| 2007/0233207 A1* | 10/2007 | Poirrier | A61M 21/00 607/88 |
| 2008/0062682 A1 | 3/2008 | Hoelen | |
| 2008/0193664 A1 | 8/2008 | Gonzalez | |
| 2008/0233053 A1* | 9/2008 | Gross | A61K 9/0048 514/1.1 |
| 2008/0262575 A1* | 10/2008 | Aunio | A61M 21/00 607/88 |
| 2010/0004499 A1 | 1/2010 | Brigatti | |
| 2010/0324631 A1 | 12/2010 | Tass | |
| 2011/0060266 A1 | 3/2011 | Streeter | |
| 2011/0077548 A1* | 3/2011 | Torch | A61B 3/112 600/558 |
| 2011/0181832 A1 | 7/2011 | Smith | |
| 2011/0295345 A1 | 12/2011 | Wells | |
| 2011/0319878 A1 | 12/2011 | DiMauro | |
| 2012/0215291 A1 | 8/2012 | Pugh | |
| 2013/0066404 A1 | 3/2013 | Tapper | |
| 2013/0201285 A1 | 8/2013 | Mao | |
| 2014/0313716 A1 | 10/2014 | Lang | |
| 2014/0330129 A1* | 11/2014 | Grenon | A61B 5/0082 600/473 |
| 2014/0358199 A1 | 12/2014 | Lim | |
| 2014/0376232 A1 | 12/2014 | Behr | |
| 2015/0005750 A1* | 1/2015 | Kelleher | A61F 9/00802 606/3 |
| 2016/0106950 A1* | 4/2016 | Vasapollo | A61B 5/0478 600/27 |
| 2016/0263395 A1 | 9/2016 | Siegel | |
| 2016/0342206 A1* | 11/2016 | Shazly | A61B 5/1114 |
| 2017/0087017 A1 | 3/2017 | Iseli | |
| 2017/0296051 A1 | 10/2017 | Kislinger | |
| 2018/0021032 A1 | 1/2018 | DiMauro | |
| 2018/0104514 A1* | 4/2018 | Gertner | A61N 7/00 |
| 2018/0188556 A1* | 7/2018 | Portney | G02C 7/06 |
| 2018/0193364 A1 | 7/2018 | Li | |
| 2018/0264284 A1* | 9/2018 | Alvarez | A61N 5/0618 |
| 2019/0106543 A1 | 4/2019 | Chintapalli | |

OTHER PUBLICATIONS

Bartels, "The neural correlates of maternal and romantic love", NeuroImage (2004), vol. 21, pp. 1155-1166.

Blanco, Improving executive function using transcranial infrared laser stimulation. Journal of Neuropsychol., Nov. 28, 2016, published in final form Mar. 2017, vol. 11, Issue 1, pp. 14-25.

Byrnes, "Light Promotes Regeneration and Functional Recovery and Alters the Immune Response After Spinal Cord Injury", Lasers Surg. Medicine, 2005, 9999, pp. 1-15.

Byrnes, "Light promotes regeneration and functional recovery and alters the immune response after spinal cord injury", Lasers Surgery Medicine, Mar. 2005, vol. 36, Issue 3, pp. 171-185, (Abstract).

Byrnes, "Low Power Laser Irradiation Alters Gene Expression of Olfactory Ensheathing Cells in Vitro", Lasers Surg Med., Aug. 2005, vol. 37, issue 2, pp. 161-171, (Abstract).

Cho, "Effect of Low-level Laser Therapy on Osteoarthropathy in Rabbig", In Vivo, Sep.-Oct. 2004. vol. 18, Issue 5, pp. 585-591.

Fahim, "Orbitofrontal dysfunction in a monozygotic twin discordant for postpartum affective psychosis: a functional magnetic resonance imaging study", Bipolar Disorders 2007, vol. 9, pp. 541-545.

Geneva, "Photobiomodulation for the treatment of retinal diseases: a review", Int. J. Ophthalmol., Jan. 18, 2016, vol. 9, Issue 1, pp. 145-152.

Gorbatenkova, "Reactivation of superoxide dismutase by the helium-neon laser irradiation", Biofizika, Jul.-Aug. 1998, vol. 33, Issue 4, pp. 717-719 (Abstract).

Kamanli, "Plasma lipid peroxidation and antioxidant levels in patients with rheumatoid arthritis", Cell Biochem. Func. 2004, vol. 22, pp. 53-57.

Karu, "Suppression of Human Blood Chemiluminescence by Diode Laser Irradiation At Wavelengths 660, 820, 880 or 950 nm", Laser Ther., 1993,vol. 5, pp. 103-109.

Keedy, "An overview of intracranial aneurysms", McGill Journal of Medicine, 2006, vol. 9, Issue 2, pp. 141-146.

King, "Doing the right thing: A common neural circuit for appropriate violent or compassionate behavior", NeuroImage, 2006, vol. 30, pp. 1069-1076.

Kringelbach, "A Specific and Rapid Neural Signature for Parental Instinct", PLoS One., Feb. 27, 2008, vol. 3, Issue 2, e1664, pp. 1-7.

Kroczek, Addiction Biology,"Prefrontal functional connectivity measured with near-infrared spectroscopy during smoking cue exposure", 2015 vol. 22, Issue 2. (Abstract).

Leibenluft, "Mothers' neural activation in response to pictures of their children and other children", Biol. Psychiatry, 2004, vol. 56, pp. 225-232 (Abstract).

Lenzi, "Neural basis of maternal communication and emotional expression processing during infant preverbal stage", Cereb Cortex. May 2009;vol. 19, Issue 5, pp. 1124-1133.

Leon-Carrion et all, "Functional Near-infrared Spectroscopy (fNIRS):Principles and Neuroscientific Applications", Neuroimaging-Methods, Prof. Peter Bright (Ed.), 2012, ISBN:978-953-51-0097-3, in Tech, pp. 47-74.

Leung, Treatment of Experimentally Induced Transient Cerebral Ischemia With Low Energy Laser Inhibits Nitric Oxide Synthase Activity and Up-Regulates the Expression of Transforming Growth Factor-Beta 1, Laser Surg. Med., 2002, vol. 31, pp. 283-288.

Liang, "Photobiomodulation partially rescues visual cortical neurons from cyanide-induced apoptosis", Neuroscience., May 12, 2006; vol. 139, Issue 2, pp. 639-649.

Lim, Inventor's Notes on Whole Brain Photobiomodulation with Vielight Neuro—a Transcranial-Intranasal Light Therapy Combination, Jan. 2016, pp. 8 and 16).

Lim, The Potential of Intranasal Light Therapy for Brain Stimulation, Presented at the NAALT Conference, Palm Beach Gardens, Florida, Feb. 2, 2013, pp. 1-16.

Naeser et al., Significant Improvements in Cognitive Performance Post-Transcranial, Red/Near-Infrared Light-Emitting Diode Treatments in Chronic, Mild Traumatic Brain Injury: Open-Protocol Study J. Neurotrauma 2014, vol. 31, Issue 11, pp. 1008-1017.

Manji, "Impairments of Neuroplasticity and Cellular Resilience in Severe Mood Disorders: Implications for the Development of Novel Therapeutics", Psychopharmacol Bull., 2001 Spring, vol. 35, Issue 2, pp. 5-49 , (Abstract).

Merry, "Treatment of dry Age-related Macular Degeneration with Photobiomodulation", presented at ARVO, Fort Lauderdale, FL, May 7, 2012.

Minagawa-Kawai, "Prefrontal activation associated with social attachment: Facial-emotion recognition in mothers and infants", Cerebral Cortex, Feb. 2009, vol. 19, pp. 284-292 (Abstract).

Mochizuki-Oda, Effectsofnear-infra-redlaserirradiationonadenosine triphosphateandadenosinediphosphatecontentsofratbraintissue Neurosci. Lett. , 2002. vol. 323, pp. 208-210.

Moses-Kolks, "Serotonin 1A receptor reductions in postpartum depression: a PET study", Fertil. Steril., Mar. 2008 vol. 89, Issue 3, pp. 685-692.

Neumeister, "Effects of tryptophan depletion on serum levels of brain-derived neurotrophic factor in unmedicated patients with remitted depression and healthy subjects", Am J Psychiatry, Apr. 2005, vol. 162, Issue 4, pp. 805-807, (Abstract).

Nitschke, "Orbitofrontal cortex tracks positive mood in mothers viewing picturesof their newborn infants", NeuroImage 21 (2004) 583-592.

Noriuchi, "The Functional Neuroanatomy of Maternal Love: Mother's Response to Infant's Attachment Behaviors" Biol. Psychitary, Feb. 15, 2008, vol. 63, Issue 4, pp. 415-423, (Abstract).

(56) References Cited

OTHER PUBLICATIONS

Oron, "Ga—As (808 nm) Laser Irradiation Enhances ATP Production in Human Neuronal Cells in Culture", *Photomed Laser Surg.*, Jun. 2007, vol. 25, Issue 3, pp. 180-182. (Abstract).
Ostrakhovich, "Active Form of Oxygen and Nitrogen in Blood Cells of Patients with Rheumatoid Arthritis: Effect of Laser Therapy", *Vestn Ross Akad Med Nauk.*, 2001, vol. 5, pp. 23-27 (Abstract).
Ranote, "The neural basis of maternal responsiveness to infants: an fMRI study", *Neuroreport*, Aug. 6, 2004; vol. 15, Issue 11, pp. 1825-1829, (Abstract).
Rochkind, "Increase of neuronal sprouting and migration using 780 nm laser phototherapy as procedure for cell therapy", *Lasers Surg. Med.*, 2009, vol. 41, pp. 277-281 (Abstract).
ROELOFSs, "On the neural control of social emotional behavior", *SCAN* (2009) vol. 4, pp. 50-58.
Romm, "Action of laser radiation on the peroxide chemiluminescence of wound exudate", *Biull. Eksp. Biol. Med.* Oct. 1986 vol. 102, Issue 10, pp. 426-428 (Abstract).
Schiffer, Psychological benefits 2 and 4 weeks after a single treatment with near infrared light to the forehead: a pilot study of 10 patients with major depression and anxiety *Behav. Brain Funct.*, Dec. 2009, vol. 8; pp. 5:46.
Seifritz, "Differential sex-independent amygdala response to infant crying and laughing in parents versus nonparents", *Biol. Psychiatry*, 2003,vol. 54, pp. 1367-1375.
Tang, Photobiomodulation in the treatment of patients with noncenter-involving diabetic macular oedema *Br. J. Ophthalmol.*, Aug. 2014, vol. 98, Issue 8, pp. 1013-1015.
Tedford, "Quantitative analysis of transcranial and intraparenchymal light penetration in human cadaver brain tissue", *Lasers in Surgery and Medicine,*, 2015, vol. 47, pp. 312-322. (Abstract).
Vladimirov, "Photobiological Principles of Therapeutic Applications of Laser Radiation Biochemistry", 2004, vol. 69, Issue 1, pp. 81-90, Moscow.
Vladimirov, "Photoreactivation of Superoxide Dismutase by Intensive Red (Laser)Light", *Free Rad. Biol. Med.*, 1988, vol. 5, Issues 5-6, pp. 281-286.
Volotovskaia, "Antioxidant action and therapeutic efficacy of laser irradiation of blood in patients with ischemic heart disease", *Vopr Kurortol Zizioter Lech Fiz Kult* May-Jun. 2003 vol. 3, pp. 22-25 (Abstract).
Wada, "Lithium: potential therapeutics against acute brain injuries and chronic neurodegenerative diseases", *J Pharmacol Sci.* Dec. 2005; vol. 99, Issue 4, pp. 307-321, (Abstract).
Wang, "Lithium Inhibition of Protein Kinase C Activation-Induces Serotonin Release", (*Psychopharmacology* (*Berl*). 1989. vol. 99, Issue 2, pp. 213-218., (Abstract).
Wollman, "In vitro cellular processes sprouting in cortex microexplants of adult rat brains induced by low power laser irradiation", *Neurol. Res.*, 1998, vol. 20, pp. 470-472.
Wollman, In vitro cellular processes sprouting in cortex microexplants of adult rat brains induced by low power laser irradiation *Neurol. Res.* Jul. 1998, vol. 20, Issue 5, pp. 470-472 (Abstract).
Wollman, Low power laser irradiation enhances migration and neurite sprouting of cultured rat embryonal brain cells *Neurol. Res.* Oct. 1996, vol. 18, Issue 5, pp. 467-470 (Abstract).
Wong-Riley, "Light-emitting Diode Treatment Reverses the Effect of TTX on Cytochrome Oxidase in Neurons", *Neuroreport*, 2001, vol. 12, Issue 14, pp. 3033-3037.
Wong-Riley, "Photobiomodulation Directly Benefits Primary Neurons Functionally Inactivated by Toxins", *J Biol Chem.*, Feb. 11, 2005 vol. 280, Issue 6, pp. 4761-4771.
Wong-Riley,"Photobiomodulation directly benefits primary neurons functionally inactivated by toxins: role of cytochrome c oxidase", *J. Biol. Chem.* 2004, e-pub Nov. 22.
Yaroslavsky, "Optical properties of selected native and coagulated human brain tissues in vitro in the visible and near infrared spectral range", *Phys. Med. Biol.*, 2002, vol. 47, pp. 2059-2073.
Zhang, "Low-Power Laser Irradiation Inhibiting $A\beta_{25-35}$-induced PC12 Cell Apoptosis via PKC Activiation" *Cell Physiol Biochem.*, 2008, vol. 22, Issue 1-4, pp. 215-222.
[No Author Listed]—Radian Thermal Products, "White Paper: Heat Pipes & Vapor Chambers", Nov. 2014, 9 pages, https://www.radianheatsinks.com/wp-content/uploads/2017/07/Heat-Pipes-and-Vapor-Chambers.pdf.
[No Author Listed]—"Point-of-care Concussion Therapy", Office for Technology Commercialization, University of Minnesota—Driven to Discover, Technology #20180342, 2018, Regents of the University of Minnesota, 3 pages.
[No Author Listed]—"Vielight: The Future of Brain Photobiomodulation", https://vielight.com/brain-photobiomodulation-devices/, Vielight, Inc., accessed Jan. 10, 2020, 11 pages.
[No Author Listed]—"MedX Health for Concussions: Rehab Laser Console System", https://medxhealth.com/en/product-rehab-console/, accessed Jan. 20, 2020, 4 pages.
Aurora CTS, Aurora Concussion Therapy Systems, Inc.—"Helping the brain heal faster", Home Page http://aurora-cts.com/,accessed Jan. 10, 2020, 1 page.
Bozkurt, "Safety Assessment of Near Infrared Light Emitting Diodes for Diffuse Optical Measurements", Biomedical Engineering OnLine, 2004, 3:9, 10 pages.
Cassano et al., "Near-Infrared Transcranial Radiation for Major Depressive Disorder: Proof of Concept Study", Psychiatry J. 2015, 352979, pp. 1-8.
Hamblin—"Shining light on the head: Photobiomodulation for brain disorders", BBA Clinical, Volumn 6 (2016), Oct. 1, 2016, pp. 113-124, published by Elsevier B.V.
International Searching Authority—International Search Report and Written Opinion for International Application No. PCT/US2018/013081, dated Apr. 5, 2018, 9 pages.
Salehpour et al.—"Brain Photobiomodulation Therapy: a Narrative Review", Molecular Neurobiol (2018) Volumn 55, Issue 8, pp. 6601-6636, Published online Jan. 11, 2018, Springer Science-Business Media, LLC, part of Springer Nature 2018.
Uozumi et al.—"Targeted Increase in Cerebral Blood Flow by Transcranial Near-Infrared Laser Irradiation", Lasers in Surgery and Medicine, Volumn 42, Issue 6, Aug. 2010, pp. 566-576, Published by ResearchGate.
Frontal Sinus Transillumunation Video, 2010, http://www.youtube.com/watch?v=8Lo3bENDqzs
International Searching Authority—International Search Report and Written Opinion for International Application No. PCT/US2020/053510, dated Jul. 27, 2020, 20 pages.

\* cited by examiner

FIG. 26
FIG. 27
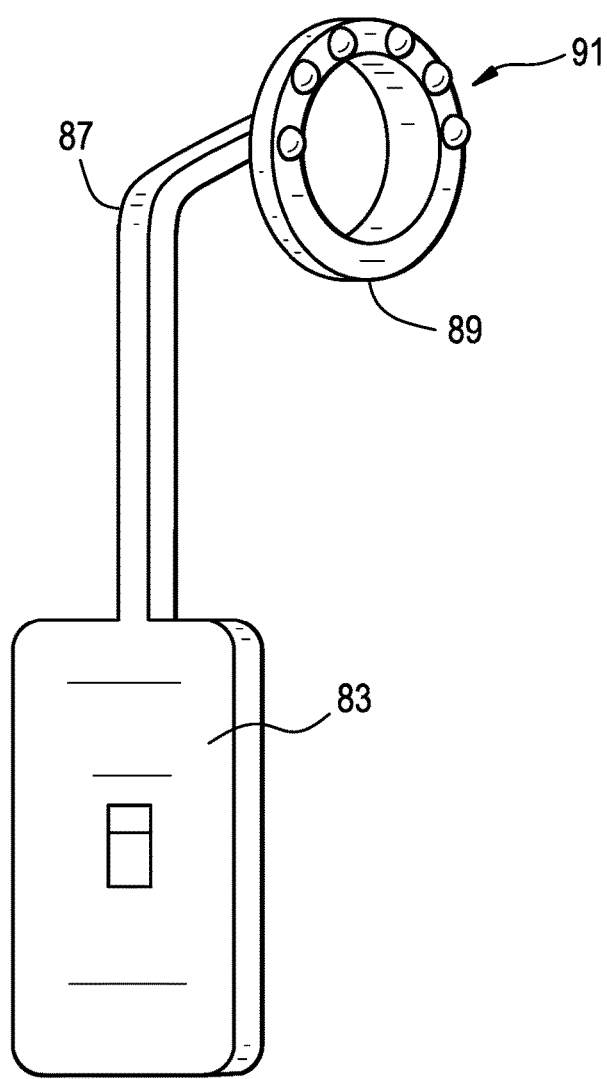
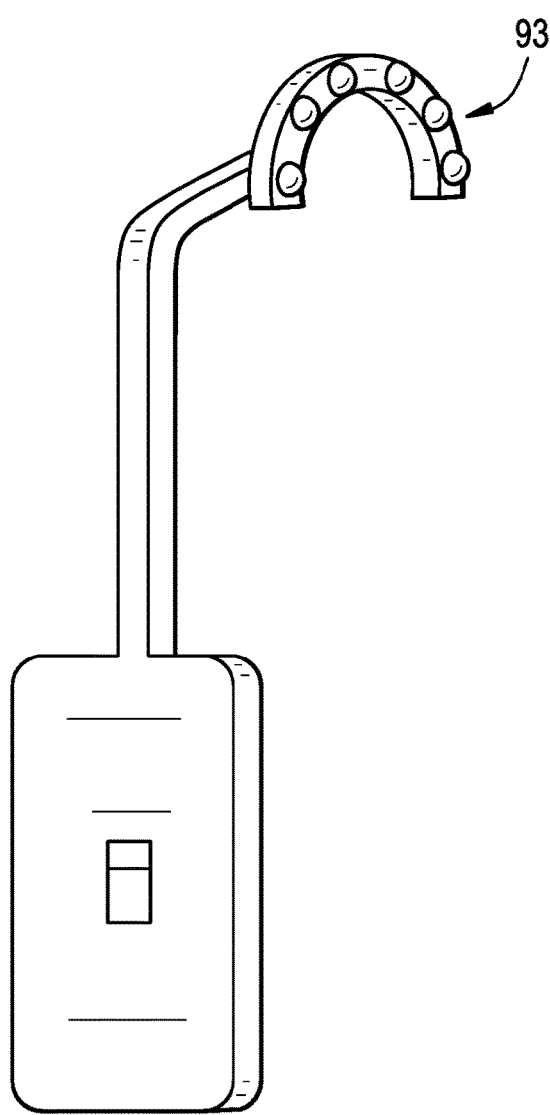

TRANS-ORBITAL INFRARED LIGHT THERAPY

CONTINUING DATA

This patent application claims priority from patent application U.S. Ser. No. 62/445,304, entitled "Trans-Orbital Infrared Light Therapy (DiMauro et al.), filed Jan. 12, 2017, the specification of which is incorporated by reference in its entirety.

BACKGROUND OF THE INVENTION

US Published Patent Application 2014-0358199 (Lim) discloses the intranasal delivery of the infrared light to the orbitofrontal cortex of the brain. The commercial embodiment of this application appears to be the Vielight 810® device. The Vielight 810® device comprises an infrared LED that is inserted into the nose and is powered by a battery pack.

Red/NIR light is significantly attenuated as it penetrates tissue. According to one Lim white paper, red/NIR light suffers a power loss of about 80% per mm penetration of tissue. (Lim, The Potential Of Intranasal Light Therapy For Brain Stimulation, Feb. 2, 2013, page 8). In another white paper, Lim reports that a) only 2.4% of infrared light penetrates 3 cm of dead tissue, and b) in live rats, only about 6% of photons with a wavelength of between 630 nm and 800 nm penetrate tissues up to 28 mm. (Lim, Inventor's Notes on Whole Brain Photobiomodulation with Vielight Neuro—a Transcranial-Intranasal Light Therapy Combination, January 2016, pages 8 and 16).

The recommended treatment time for the Vielight Intranasal device is 25 minutes. (Lim, Potential supra, abstract.)

U.S. Pat. No. 8,734,498 (Codman I) discloses a hand-held intranasal light device comprising an infrared LED powered by a battery contained within the handle of the device.

The literature reports several articles involving NIR irradiation of the forehead, with subsequent monitoring of cerebral blood flow via functional NIR spectroscopy. See, e.g., Kroczek, *Addiction Biology*, "Prefrontal functional connectivity measured with near-infrared spectroscopy during smoking cue exposure", 2015. None of the FNIR articles reviewed report on neuronal activity in the OFC, thereby implying that NIR light did not reach the OFC from irradiation of the forehead. See. also, e.g., Leon-Carrion, "Functional Near-infrared Spectroscopy (fNIRS): Principles and Neuroscientific Applications" in Neuroimaging—Methods.

SUMMARY OF THE INVENTION

It has been observed that the upper portion of the eye socket is much closer to the orbitofrontal cortex than the nostril. Whereas the typical nostril is about 10-12 cm from the anterior portion of the orbitofrontal cortex (OFC), the upper portion of the eye socket is only about 1 cm from the anterior portion of the orbitofrontal cortex (OFC). Because tissue so strongly attenuates the intensity of red/NIR light over distances of several centimeters, the reduced distances to the OFC afforded by the upper eye socket make it an attractive location for placing a red/NIR light emitting diode (LED) and providing LLLT to the OFC from that location.

Therefore, in accordance with the present invention, there is provided a method comprising:
a) placing an LED against the eyelid of a patient in a location between the upper portion of the eye and the eye socket of the patient,
b) moving the LED posteriorly so that its posterior edge sits at least 1 cm within the eyesocket, and
c) actuating the moved LED to deliver red/NIR light to the orbitofrontal cortex of the patient.

DESCRIPTION OF THE FIGURES

FIG. 26 discloses a handheld device with a LED-carrying tube.
FIG. 27 discloses a handheld device with a LED-carrying crescent.

DETAILED DESCRIPTION OF THE INVENTION

Figure 1:
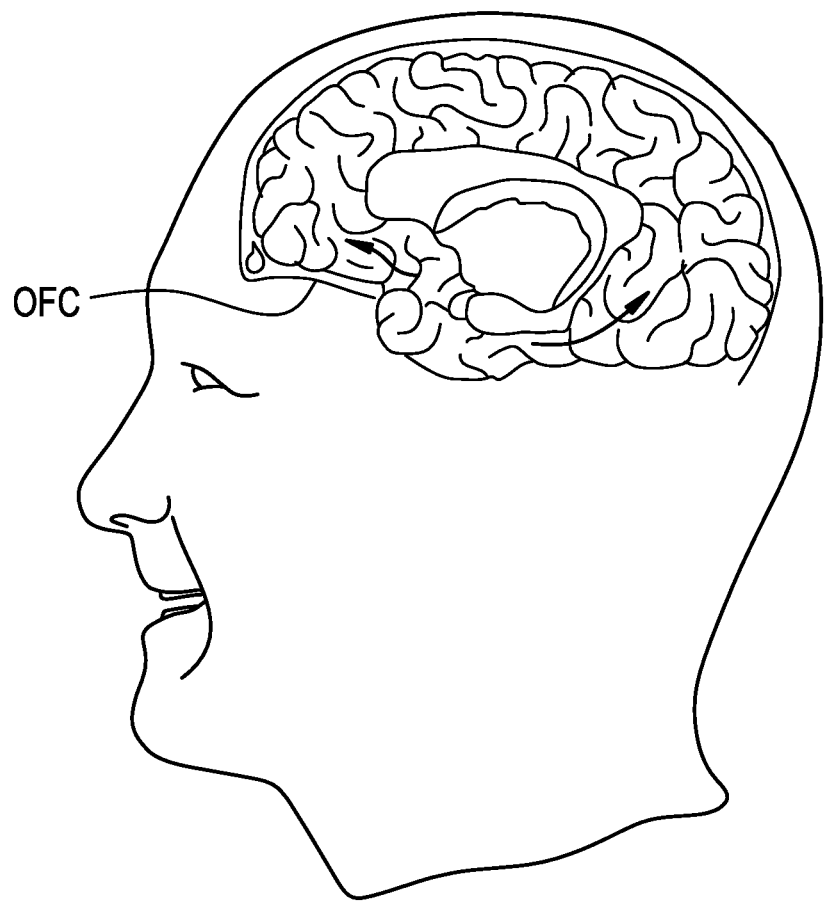
FIG. 1 is a sagittal cross-section of the human skull and brain.

Now referring to FIGS. 1-5, it can be readily seen that the upper portion of the eye socket is much closer to the orbitofrontal cortex (OFC) than the nostril. FIG. 1 in particular demonstrates that the top of the eye is about 90% closer to the orbitofrontal cortex than the nostril. Because, as discussed above, tissue so strongly attenuates the intensity of red/NIR light, the reduced distance afforded by placing an LED in the upper eye socket may allow it to provide an intensity of red/NIR light that is many-fold higher than nostril-based light delivery from a comparable device. This attractive feature may allow the clinician to deliver the same therapeutic dose to the OFC in a significantly smaller fraction of the time as nostril-based light delivery from a comparable device. Alternatively, this attractive feature may allow the clinician to deliver a higher therapeutic dose to the OFC in the same amount of time as nostril-based light delivery from a comparable device.

Figure 2:
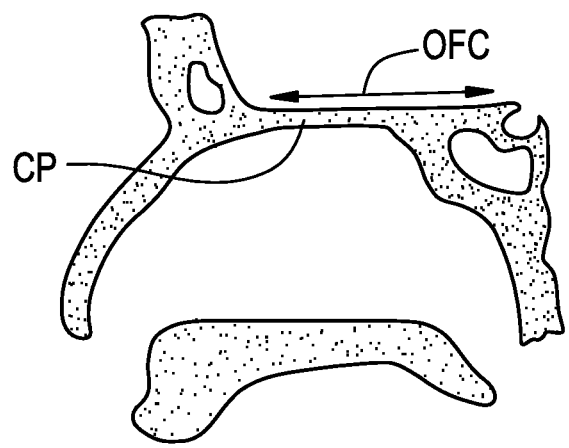
FIG. 2 is a sagittal cross-section of the human nasal cavity.

FIG. 2 reveals the thin nature of the cribriform plate CP tissue layer lying beneath the OFC. Although this CP tissue must be traversed by the light originating from the eye socket in order to reach the OFC, its thin nature should not cause much attenuation of the red/NIR light.

Figure 3:
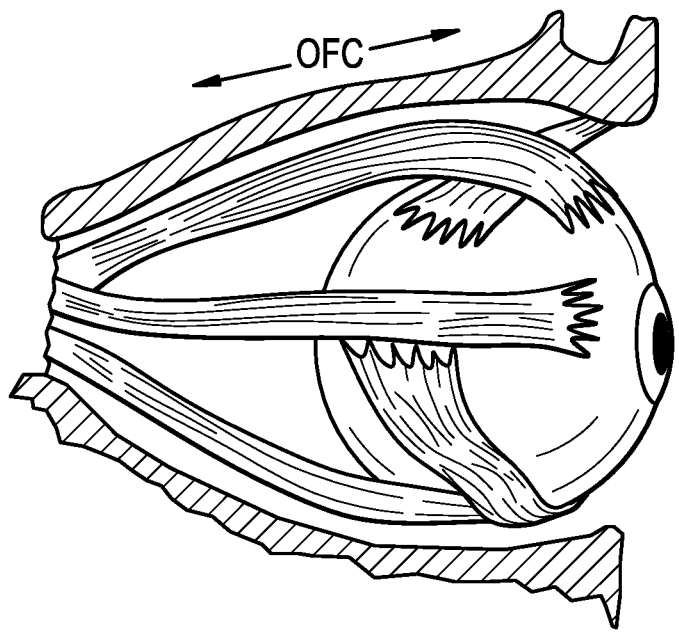
FIGS. 3-4 are sagittal cross-sections of the human eye and its relation to the OFC.
Figure 4:
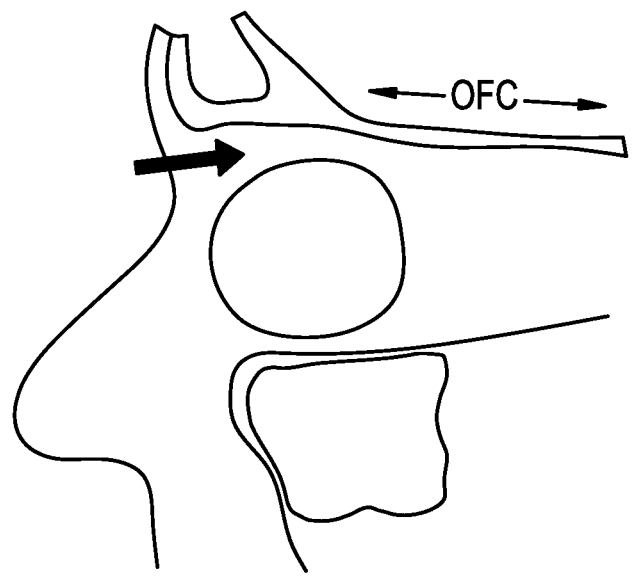

FIG. 3 discloses a sagittal cross-section of the eye socket, in which the significant space between the upper portion of the eye and the eye socket is clearly demonstrated. This space is filled only by a few muscles (shown), with the remainder being essentially fatty tissue (not shown). It has been found that a cylindrical tube having a diameter substantially equivalent to the eye socket (e.g., about 5 cm) and a thickness of about 2 mm can comfortably fit into this space to a depth of about 2 cm (20 mm) from the outer rim of the eye socket. The extent to which an LED situated at the distal end of such a tube can comfortably penetrate the eye socket space is shown by the arrow → in FIG. 4.

Figure 5:
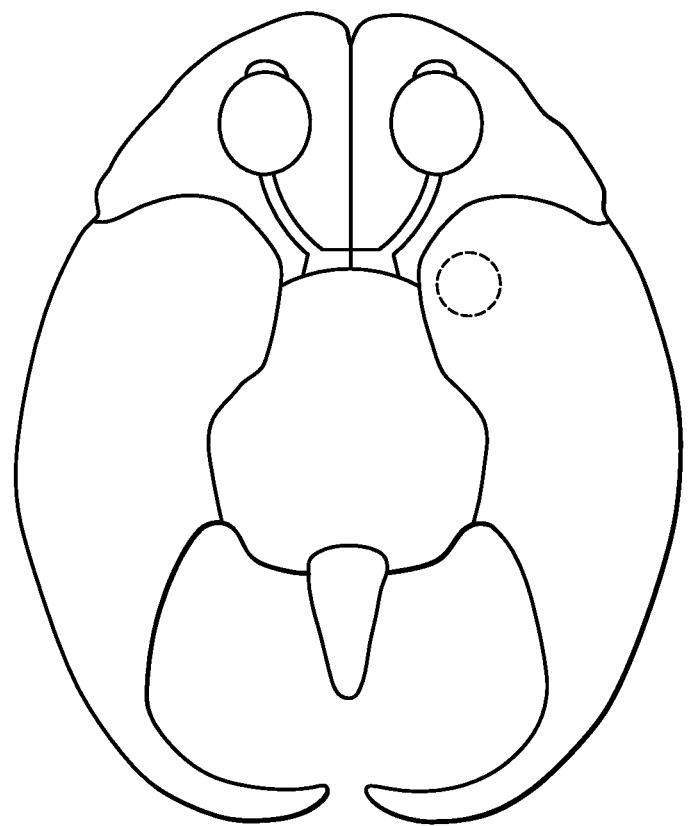
FIG. 5 is a bottom view of the human brain.

FIG. 5 is a bottom view of the brain showing the relative location of the eyes and the OFC. As shown, it is clear that the placing an LED between the eye socket and upper eye affords a tremendous advantage is delivering red/NIR light to the OFC in both the anterior-posterior and medial-lateral directions.

Figure 6:
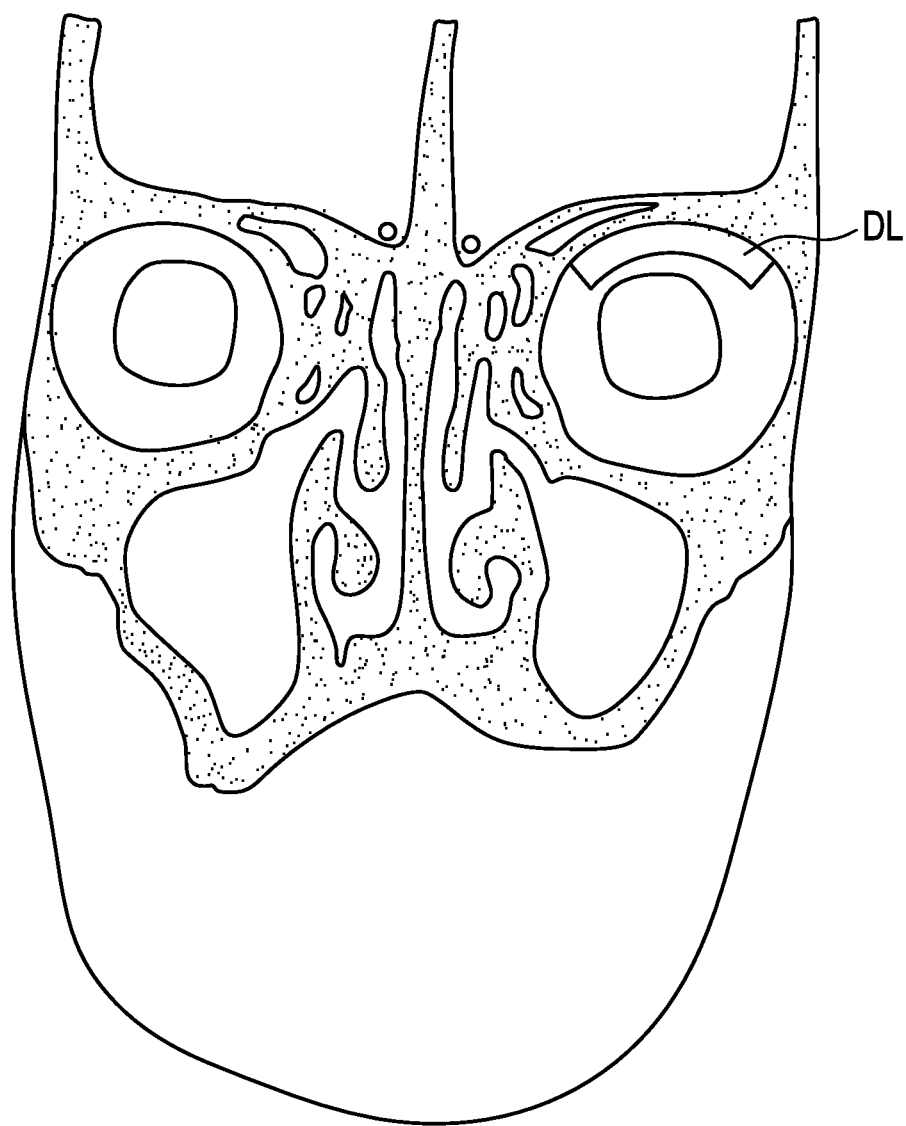
FIG. 6 is a frontal view of the human skull having an LED device placed in the upper eye socket.

FIG. 6 is a frontal view of the skull of a patient in which the desired location (DL) of LEDs situated on a cylindrical tube is disclosed.

In general, it is believed that the devices adapted to deliver red/NIR light through the eyelid preferably comprise:
a) a flexible nose bridge 1,
b) an orbital rim 3 shaped to encircle an eye and attached to the bridge, and
c) a red/NIR light-emitting unit 5 (such as an LED) attached to the rim (preferably in a location posterior to the rim) and adapted to emit light posteriorly.

The flexible nose bridge preferably has a spring-like quality that allows it to fit snugly to the bridge of the patient's nose. It functions to keep the rim (and hence the LED) in its desired location, while comfortably allowing the patient or clinician to easily adjust the bridge's location up or down on the nose. Simply, the patient flexes the bridge slightly open while finding the optimum placement of the rim/LED unit in the eye socket and then releases the bridge once that location is found in order to lock the device in the desired location. In some embodiments, the flexible nose bridge comprises a shape memory material that has a memorized shape that provides a snug fit, and is preferably a shape memory metal such as nitinol.

In some embodiments, the rim of the device has a shape and size and is fitted on the nose such that the inner portion of the upper eye socket hangs below the rim of the device. In these cases, a cylindrical tube 7 having an LED 9 attached to its distal end portion 11 is preferably selected as the light-emitting unit, and this tube is delivered through the rim of the glasses so that the so-inserted tube fits into the space between the upper eye and the upper eye socket. The rim and tube can be threadably connected by a thread 13 to afford the patient/clinician additional selective depth control of the tube/LED placement within the eye socket.

Now referring to FIGS. 7-11, there is provided a light therapy device comprising:
a) an eyeglasses superstructure comprising:
i) a flexible nose bridge 1,
ii) first and second rims 3 bilaterally extending from the nose bridge,
iii) first and second temple bars 15 respectively extending from the rims, the bars having posterior tips,
b) a cap 6 comprising i) a tubular portion 7 having a threaded outer surface and a posterior (distal) surface,
ii) at least one LED 9 located on the posterior (distal) surface of the tube, and iii) a proximal base,
wherein the cap extends through the first rim.

Figure 7:
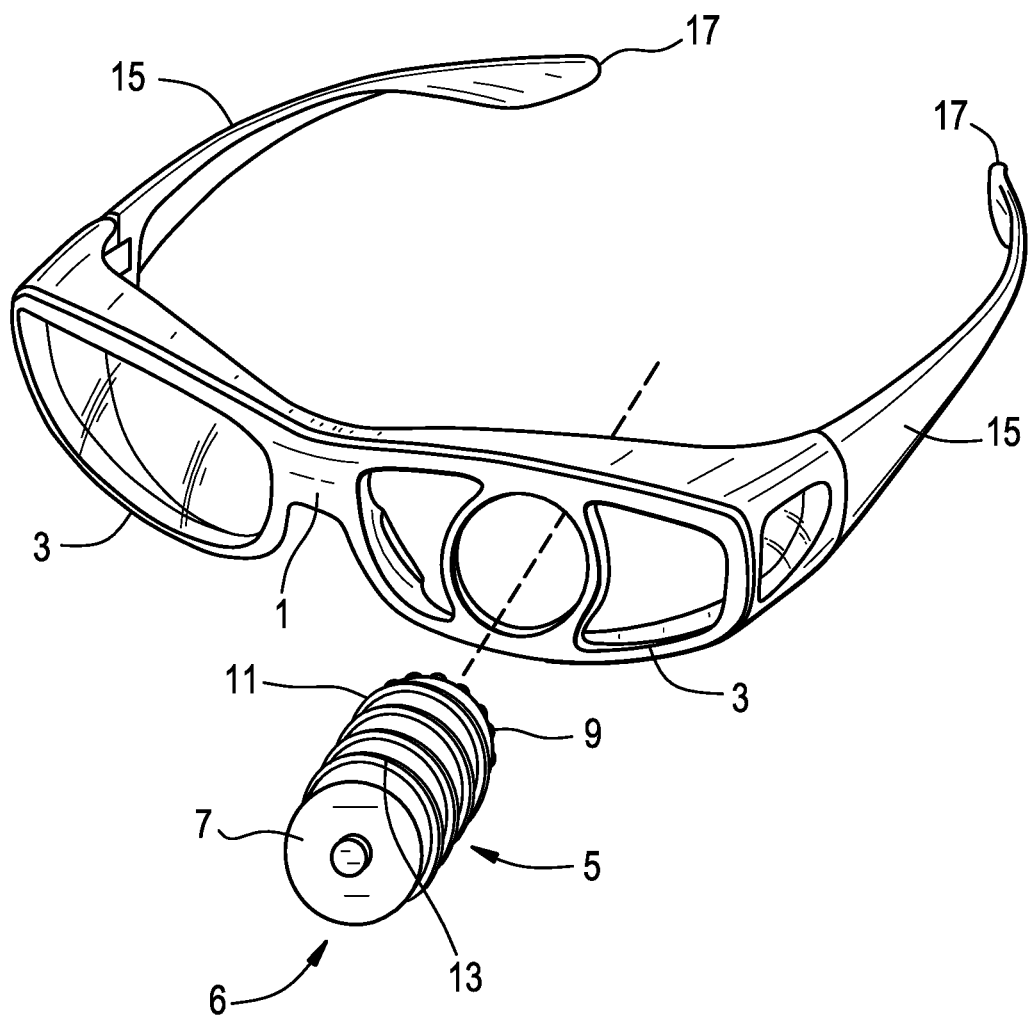
FIG. 7 is an exploded view of a tube-based LED device set in an eyeglass frame.

FIG. 7 is an exploded view of the device, demonstrating how the cap 6 is intended to be threadably delivered distally through the first rim (whose mating threads are not shown). Once the patient is satisfied with the cap placement within the eye socket, the flexible nose bridge can be released and the device position locked in place. The curved tips 17 of the temple bars help maintain the desired position while affording the patient a comforting measure of familiarity, in that the device looks somewhat like a standard pair of eyeglasses.

Figure 8:
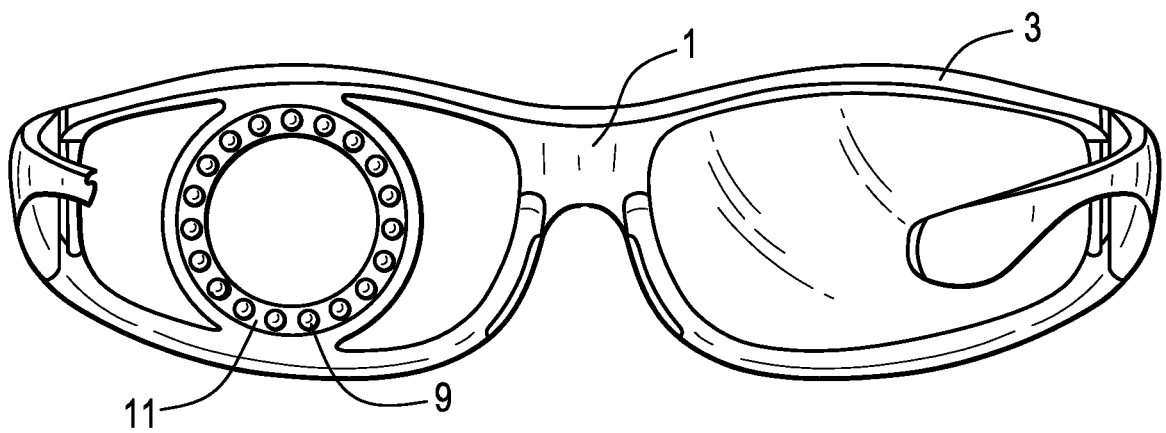
FIG. 8 is a rear view of a tube-based LED device set in an eyeglass frame.

FIG. 8 is a back view of the device, showing the LEDs positioned on the distal end portion of the cap, while the cap is inserted through the first rim of the eyeglass unit.

Figure 9:
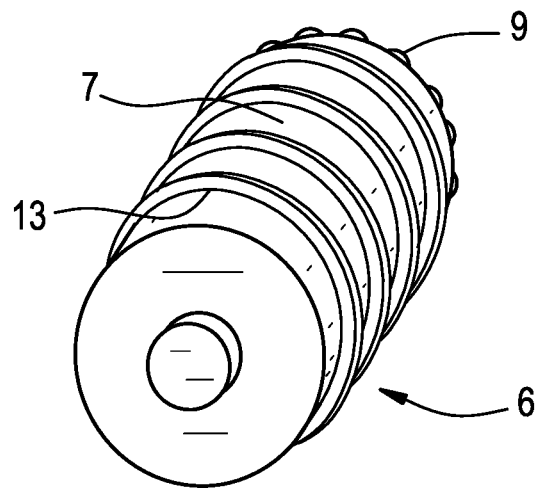
FIG. 9 is a perspective view of a tube-based device having distal LEDs.

FIG. 9 is a perspective view of the cap, showing the thread on the outer radial tubular surface of the device. This threads mates with a thread provided on the inner surface of the first rim (not shown) so as to provide a threadably-controlled delivery of the LEDs into the space between the eye socket and the upper portion of the eye. FIG. 9 further discloses a push-button actuator located in the center of the base. This provides the patient with an easy means of turning the LED component of the device on and off.

Figure 10:
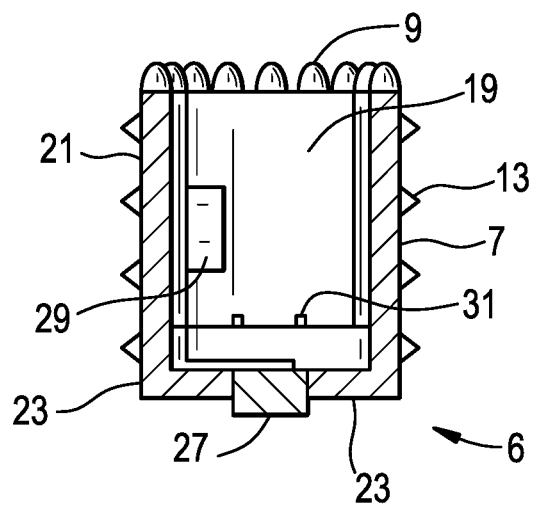
FIG. 10 is a cross-section of the tube device of FIG. 9.

FIG. 10 discloses a cross-section of a preferred cap comprising:
a) a tube 7 having a bore 19, a threaded outer surface 21, a proximal end portion 23 and a distal end portion 11,
b) a base 25 attached to the proximal end portion of the tube,
c) a plurality of LEDs 9 attached to the distal end portion of the tube,
d) an actuator 27 extending through the base,
e) a battery supply 29 situated in the bore and electrically connected to the actuator and the LEDs.

In use, this cap is threadably delivered through the rim so that at least the upper portion of the distal end portion of the cap enters into the eye socket. The lower portion of the cap can either enter the lower portion of the eye socket or (if a slightly over-sized cap is used) rest comfortably upon the cheek bone.

FIG. 10 cap also includes a white light LED 31 located inside of the cap. This white light LED is also electrically connected to the actuator and battery so as to serve as a check indicator to the patient that the circuitry is working and that the therapeutic LEDs located at the distal end of the cap are turned on.

Figure 11:
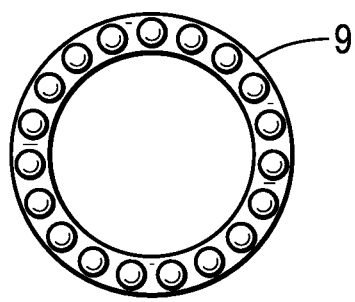
FIG. 11 is a distal view of the device of FIG. 9.

FIG. 11 discloses a plurality of LEDs 9 substantially uniformly distributed about the perimeter of the distal end portion 11 of the tube portion of the cap. Having such as uniform distribution means that sufficient LEDs will always be on the upper half of the device no matter the rotation so as to provide sufficient irradiation of the OFC, and so allows the patient to concentrate solely on finding the proper and comfortable depth of the cap in the eye socket.

Figure 12:
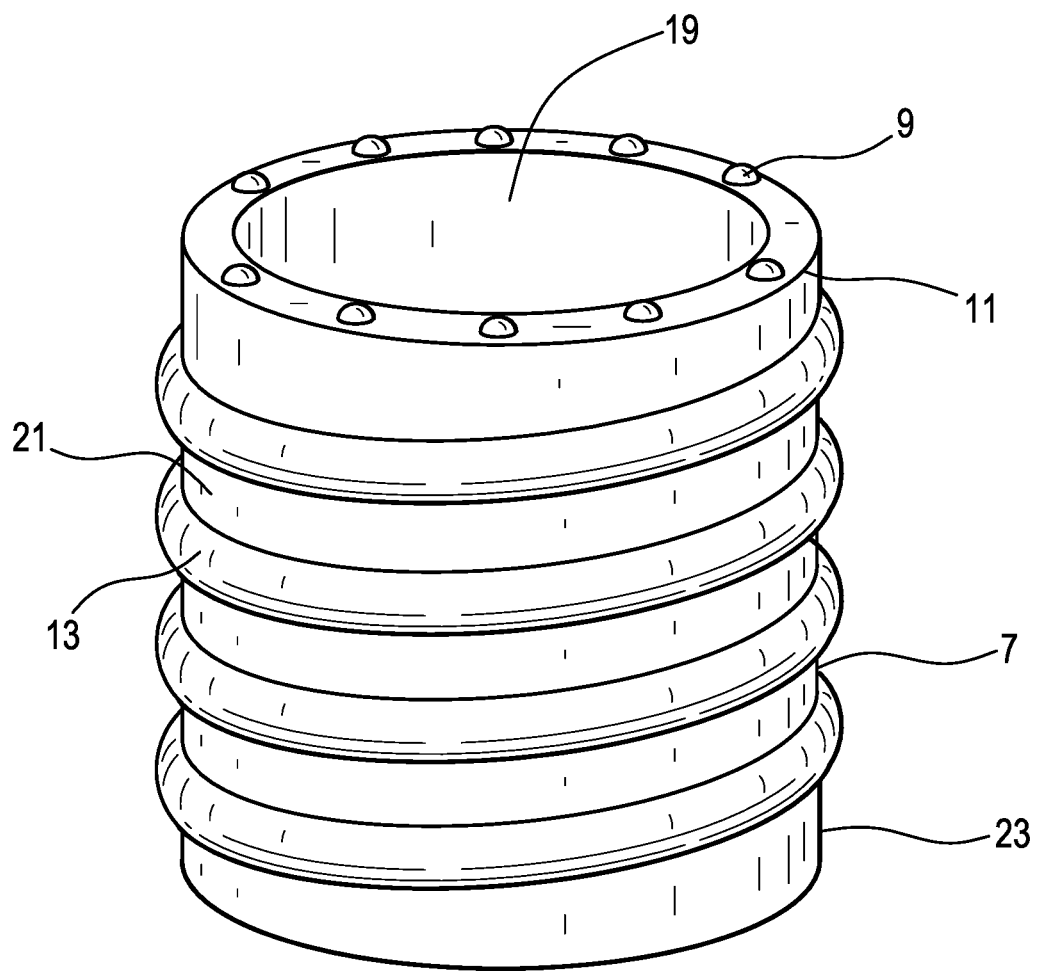
FIG. 12 is a view of a tube-based LED device having coils for coupling with near field communications systems.

FIG. 12 discloses another cap for irradiating the OFC, comprising:
a) a tube 7 having a bore 19, a distal end portion 11, a proximal end portion 23 and a threaded outer surface 21, wherein the threaded outer surface comprises a metallic thread 13,
b) a plurality of LEDS 9 located at the distal end portion of the tube,
wherein the LEDs are electrically connected to the metallic thread.

The advantage of the FIG. 12 design lies in its use of a metallic thread electrically connected to the LEDs. The metallic thread is also an energy receiving coil. This design provides an opportunity to deliver power to the LEDs through the coil, thereby avoiding the need for batteries. In some embodiments, the coil can receive Rf energy from a nearby Rf emitter. In some embodiments, the coil can couple with a device having near field communications (NFC) capability, such as the conventional cell phone. Because cell phone NFCs can deliver at least several milliwatts of power, they are particularly desirable because the cell phone electronics can be used to tailor the power delivered to the cap, including shutting off the device and timing the length of light delivery.

Figure 13:
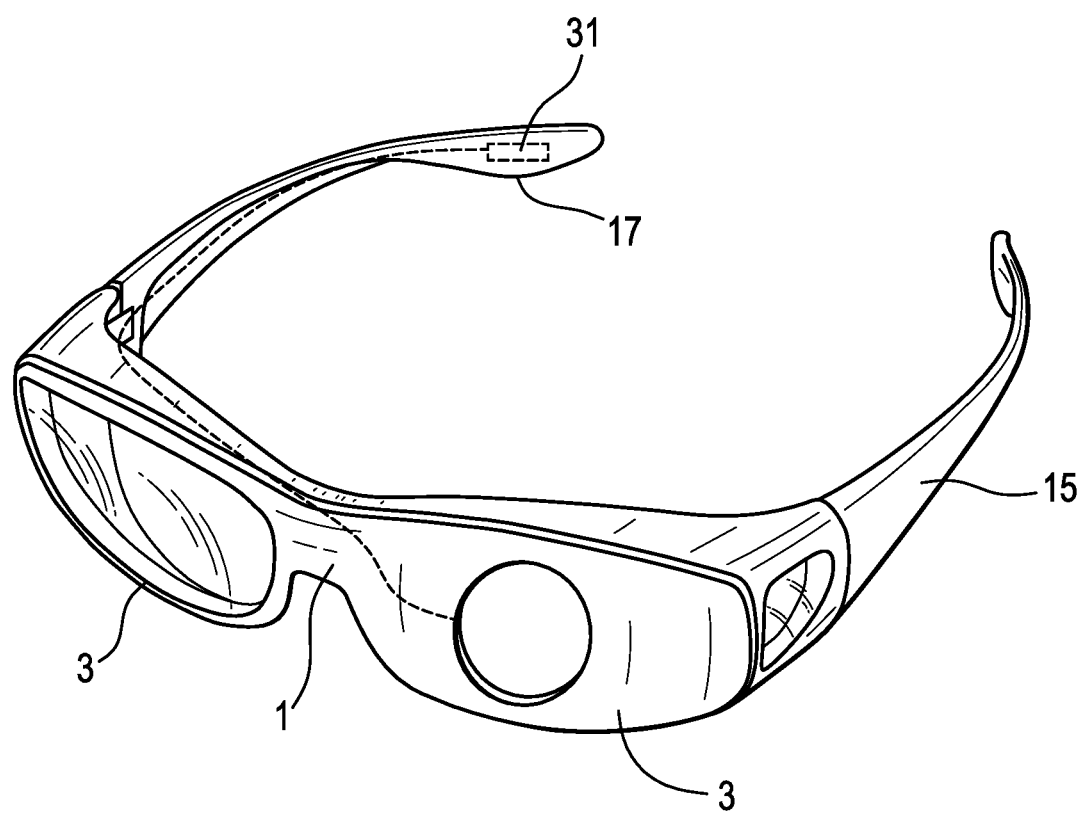
FIG. 13 is a perspective view of an eyeglass frame having batteries provided in the temple bar tip.

FIG. 13 discloses a portion of a light therapy device comprising an eyeglasses superstructure comprising:
i) a flexible nose bridge 1,
ii) first and second rims 3 bilaterally extending from the nose bridge,
iii) first and second temple bars 15, each respectively extending from the rims and having a curved tip 17,
iv) a power supply 31 (in the form of batteries) located in the curved tip of the temple bars and electrically connected to the first rim.

In some embodiments thereof, the electrical connection in the first rim comprises a metallic thread (not shown). This metallic thread in the first rim can threadably mate with a corresponding metallic thread located on the outer surface of the tube portion of the cap, which is in turn in electrical connection with the LEDs. Hence, once this cap inserted into the rim, an electrical connection between the power supply and the LEDs is made, and power is provided to the LEDs. An on/off switch actuating the batteries can also be provided in the curved tips of the temple bars.

Generally, the dimensions of the tube that carries the LEDs are such that the tube comfortably fits in the eye socket. Preferably, the tube has a diameter of between about 4 cm and 6 cm, more preferably between about 4.5 cm and 5.5 cm, more preferably between about 4.7 cm and 5.3 cm. Preferably the thickness of the tube is between about 0.5 mm and 5 mm, more preferably between about 1 mm and 4 mm, more preferably between about 2 and 3 mm. In some embodiments, the tube is dimension so that the upper portion of the tube comfortably fits in the upper portion of the eye socket and the lower portion of the tube rests upon the outer rim of the eye socket. In some embodiments, the tube also has a transparent material attached to the distal end portion thereof, wherein the transparent material encases the LEDs.

In some embodiments, the eyeglass-based devices use LEDs on a single side of the eyeglasses. This allows the user to see out the other eye during treatment, thereby enhancing compliance. In other embodiments, however, LEDs are provided on each side of the eyeglasses. The bilateral LEDs have the advantage of providing greater coverage of the OFC.

In some embodiments, the rim of the device has a shape and size such that the inner portion of the upper rim of the eye socket is above the rim of the device. In these cases, a semi-cylindrical crescent having an LED attached to its distal end portion is preferably used, and this crescent is slidably delivered along the upper surface of the rim of the glasses.

Figure 14A:
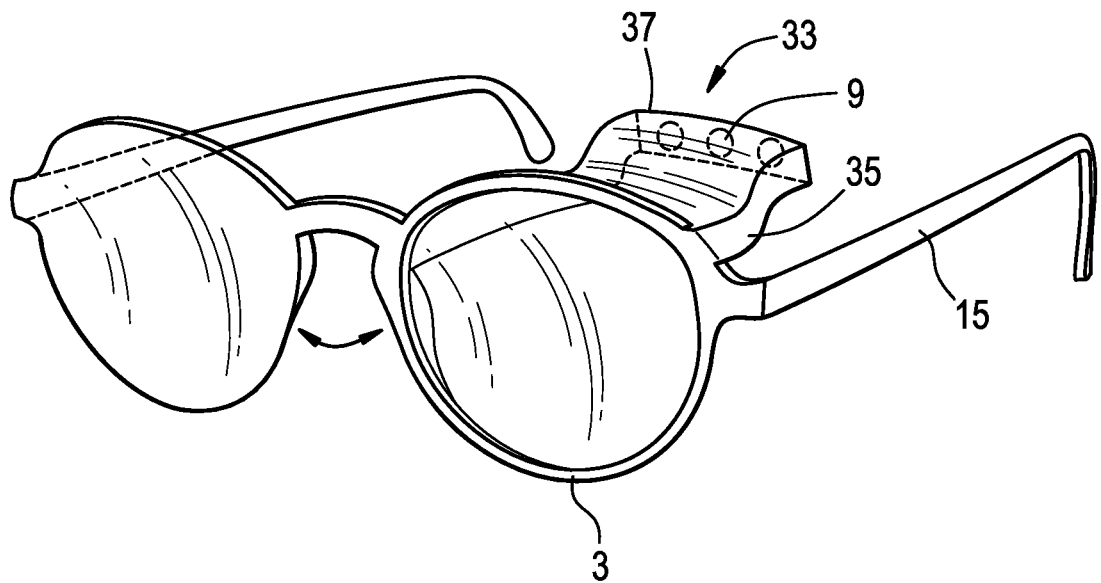
FIG. 14A is a perspective view of a LED device set in an eyeglass frame, wherein the nose bridge is flexible.
Figure 14B:
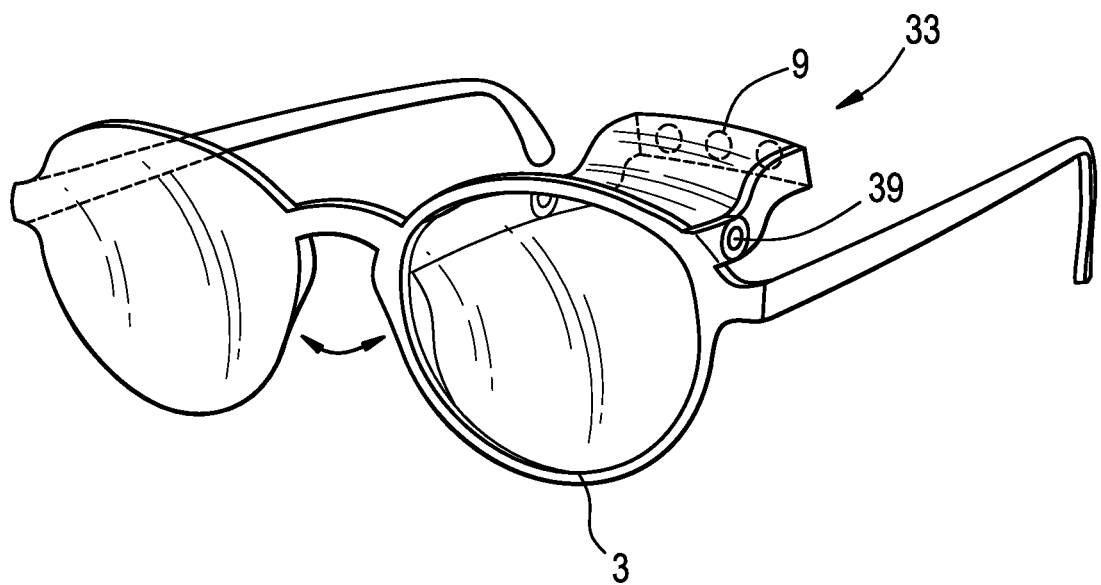
FIGS. 14B-F are various goggle related embodiments.

Now referring to FIGS. 14A-B, there is provided a light therapy device comprising an eyeglasses superstructure comprising:
i) a flexible nose bridge 1,
ii) first and second rims 3 bilaterally extending from the nose bridge, each rim having an upper surface,
iii) first and second temple bars 15 respectively extending from the rims and having a curved tip,
iv) a flange 33 having an anterior end portion 35 extending posteriorly from the upper surface of the first rim and a posterior (distal) end portion 37,
v) a plurality of LEDs 9 located on the (distal) posterior end portion of the flange.

In use, the flexible nose bridge of device of FIGS. 14A-B is opened, and the device is placed on the nose and advanced posteriorly until the posterior end portion of the flange that carries the LEDs fits snugly between the upper portion of the eye and the eye socket. At this point, the nose bridge is released to lock in the LED location. The power supply may preferably be located in the flange or in the temple tips.

In FIG. 14B, the anterior end portion of the flange is pivotally connected to the rim by a hinge 39, thereby allowing for increased adjustability. In one embodiment, there is provided a set of eyeglasses having a flange extending proximally the upper portion of a first rim, wherein the first rim has a pair of bilateral posts, the anterior portion of the flange has a pair of opposing bilateral annuluses adapted to rotatably received the posts, and the posts are rotatably received in the respective annuluses. These post-annulus hinge features give the flange the ability to swivel upon the upper portion of the rim, thereby allowing the user to tailor the fitting of the flange in the space between the upper eyeball and the eye socket.

Figure 14C:
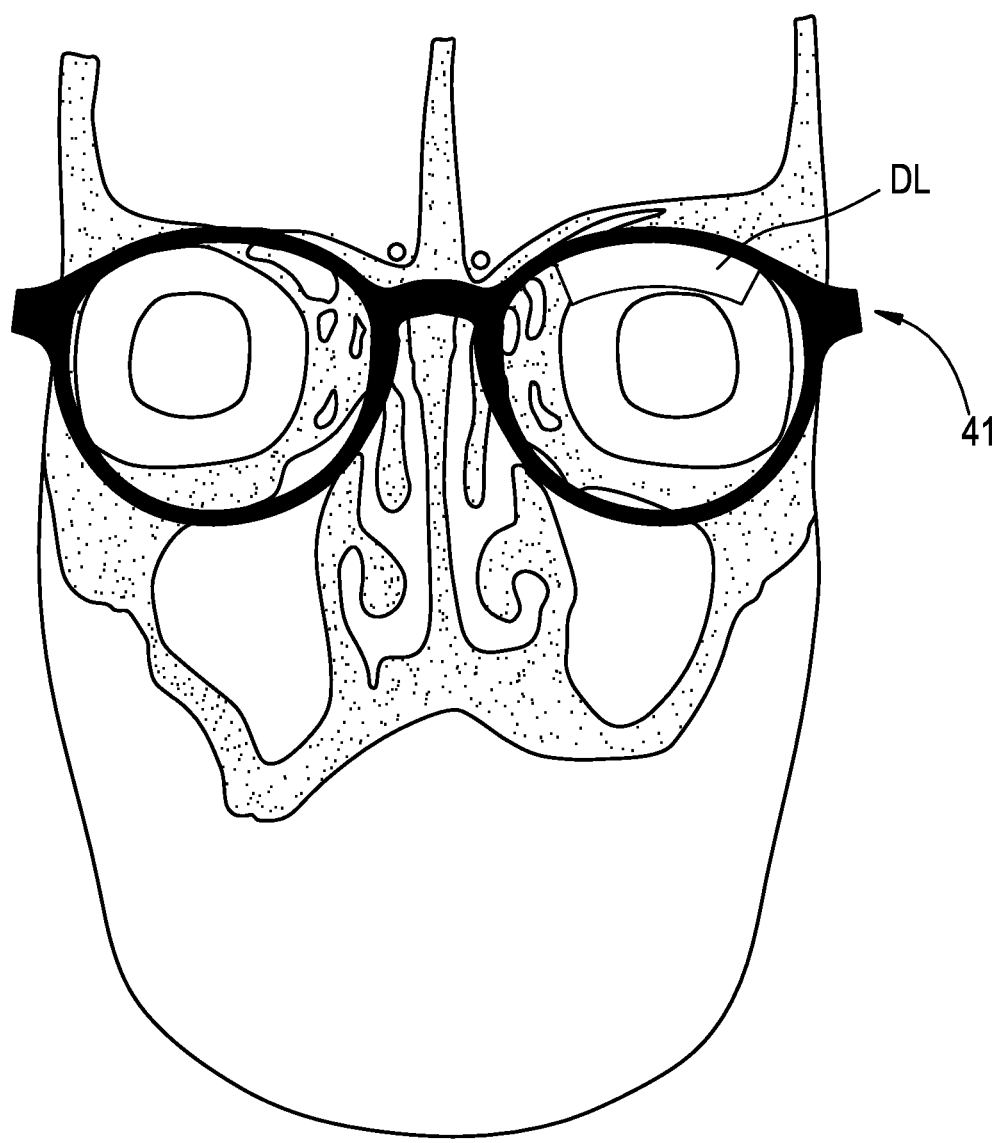

FIG. 14C shows the relationship between the glasses superstructure 41 and the desired location DL of the LED irradiation imposed on a cross-section of a skull. In one embodiment, there is provided a set of glasses whose rims are flexible and are shaped to fit into the contour of the space between the upper eyeball and the upper eye socket. The LEDS (not shown) are provided substantially on the top and posterior portions of the rim. Power for the LEDs can be provided by batteries located in the temple bars. In some embodiments, the rims are shaped to fit into the contour of the space between substantially the entire eyeball and eye socket. In some embodiments, these glasses are custom made based upon an xray taken of the patient's skull.

FIG. 14 D shows power supplies 31 located on the temple bars 15 of the glasses.

Figure 14D:
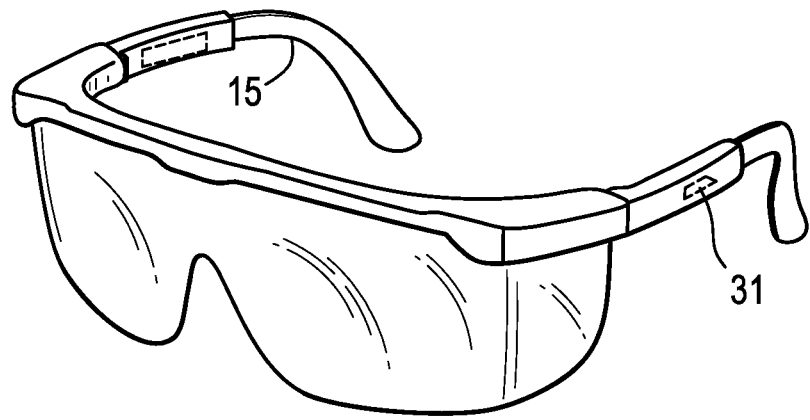
Figure 14E:
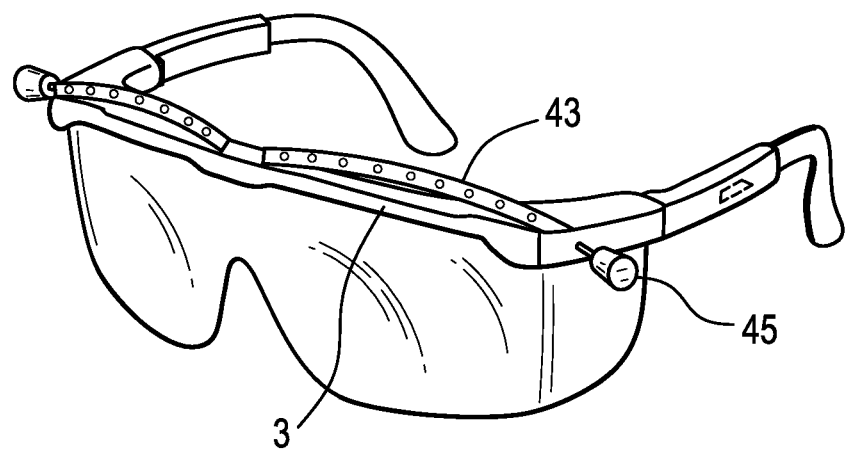

FIG. 14E shows an array 43 of LEDs located above rims 3 and which are rotatably adjustable by swivel pin 45 located in the rim.

Figure 14F:
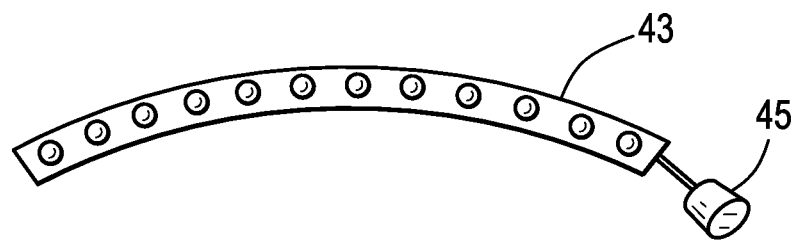

Now referring to FIGS. 14D-F, given the concerns with laser light directly into the eye, in some embodiments, there is provided goggle-like eyeglasses that fit up into the fatty space between the eye and the eye socket. In this embodiment, infrared light from the LED can be emitted from the upper frames of the glasses or goggles themselves. In some embodiments, the upper rim has a hinge (preferably, a V-hinge) wherefrom the light can be selectively adjusted to target the fatty space without the LED actually contacting the eyelid. However, given that the goggles will likely naturally fit very close to the orbital bone gap, preferably the swivel is provided flush with the frame (and not extended therefrom, where it would be lifted and pointing more to a spot above the eyebrows).

In some embodiments, the LEDs are embedded into a slightly rounded upper rim to fit the contour of the upper eye.

In some embodiments, the eyeglasses comprise bilateral rims and a pair of rotatable rods disposed about the upper portion of each rim. Each rod is embedded with a plurality of LEDs and has an adjustable knobs disposed at its lateral end that allows the user to effectively swivel the LEDs to appropriate posture vis-à-vis the upper eye socket. The bilateral temple bars may optional hold batteries (as power supply) and/or a USB port for recharging or command input. In one embodiment, the rod can be embedded in its respective rim. In another embodiment, the rod is disposed on top of the rim. In another embodiment, the rod is disposed on the inner face of the rim closer to the eye (i.e., the posterior portion of the rim).

Figure 15:
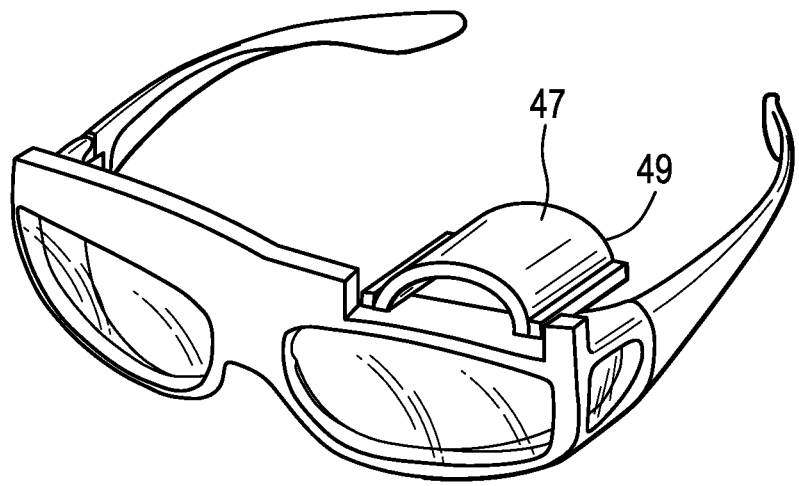
FIGS. 15-19 are various views of an embodiment in which the LED crescent is delivered above the eyeglass rim.
Figure 16:
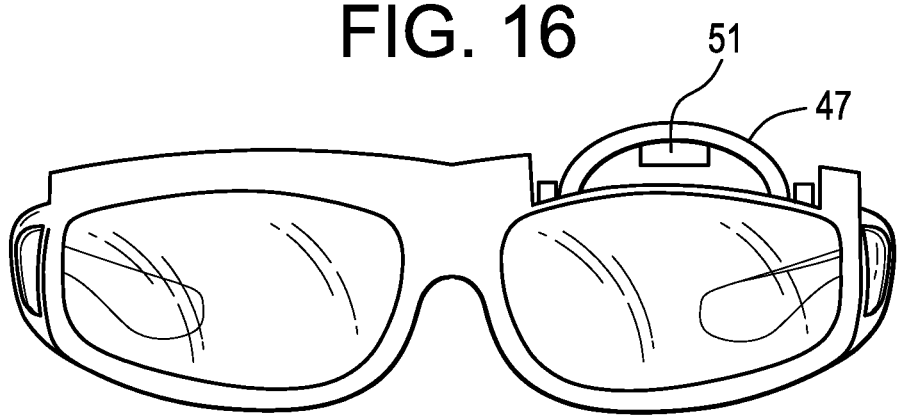
Figure 17:
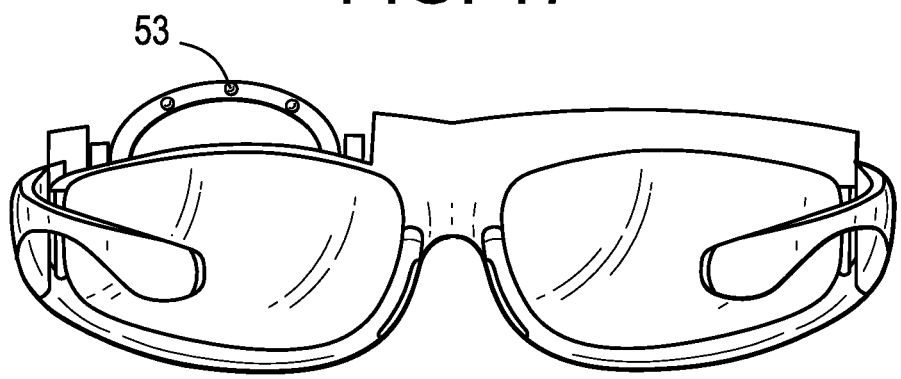

In some embodiments in which the LEDs are located above the eyeglass rims, a component substantially shaped as a crescent is used as the eye socket insert. FIGS. 15-17 disclose a portion of a light therapy device comprising:
a) an eyeglasses superstructure 41 comprising:
  i) a flexible nose bridge,
  ii) first and second rims bilaterally extending from the nose bridge, each rim having an upper surface having an anterior-posterior channel defining a pair of sidewalls,
  iii) first and second temple bars respectively extending from the rims and having a curved tip,
c) a substantially crescent 47 having a distal end portion, lateral end surfaces and a pair of rubber strips longitudinally attached to the lateral end surfaces of the crescent,
d) a plurality of LEDs 53 attached to the distal end portion 49 of the crescent,
e) a power supply 51 (in the form of batteries) disposed within the crescent and electrically connected to the LEDs,
wherein the rubber strips of the crescent flexibly contacts the sidewalls so that the crescent is slidably and selectively insertable into the channel.

Figure 18:
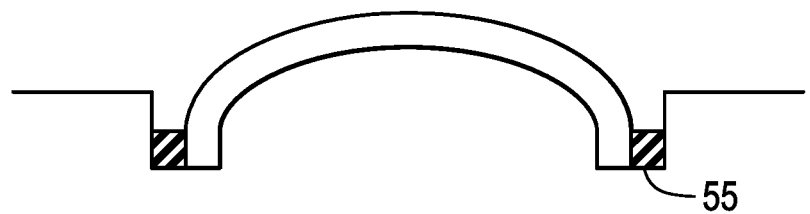

In this FIG. 15-17 design, the pair of rubber strips function as an effective O-ring that allows for slidable but secure adjustment of the depth to which the crescent extends from the rim into the eye socket. In other embodiments, as in FIG. 18, the rubber strips 55 are attached to the eyeglasses and not the crescent but provide the same slidable depth-selection function.

Figure 19:
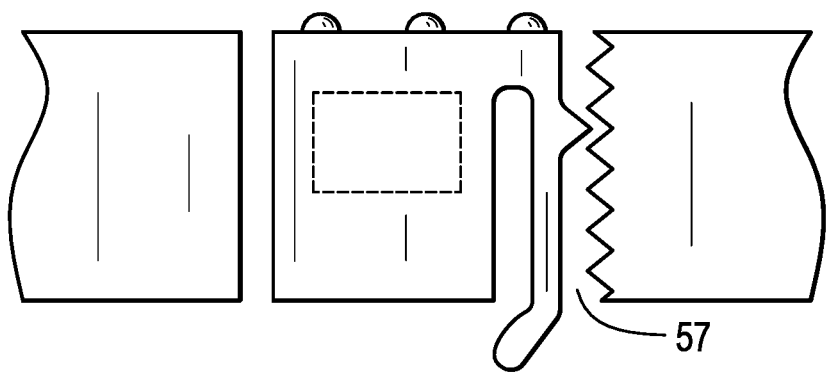

In some embodiments in which the LEDs are located above the rims, a ratchet feature is used to provide secure incremental adjustment of the substantial crescent depth upon the rims. FIG. 19 disclose a portion of a light therapy device comprising:
a) an eyeglasses superstructure comprising:
  ii) a flexible nose bridge,
  ii) first and second rims bilaterally extending from the nose bridge, each rim having an upper surface having a channel defining a pair of sidewalls, wherein at least one sidewall has a multi-toothed surface,
  iii) first and second temple bars respectively extending from the rims and having a curved tip, b) a substantially crescent having a distal end portion and lateral end surfaces, wherein a first lateral end surface comprises a flexible bar having a ratchet tooth,
c) a plurality of LEDs attached to the distal end portion of the crescent,
d) a power supply (in the form of batteries) disposed within the crescent and electrically connected to the LEDs,
wherein the flexible ratchet tooth 57 of the crescent selectively mates with the toothed surface of the channel so that the crescent is selectively and securely inserted into the channel.

In use, the user presses down on an anterior end of the flexible bar so that the crescent can slide freely within the channel. When the desired location for the crescent is found, the user releases the anterior end of the flexible bar, and the ratchet tooth of the half-tooth inserts into the multi-toothed surface of the channel, thereby locking the position of the crescent vis-à-vis the rim.

In other embodiments, the ratcheting is switched so that the flexible bar having a ratchet tooth is located on one of the sidewalls, and the crescent has the multi-toothed surface.

The term "substantial crescent" is meant to include all curved-tube portions that can fit between the upper eye socket and the upper portion of the eye.

Figure 20:
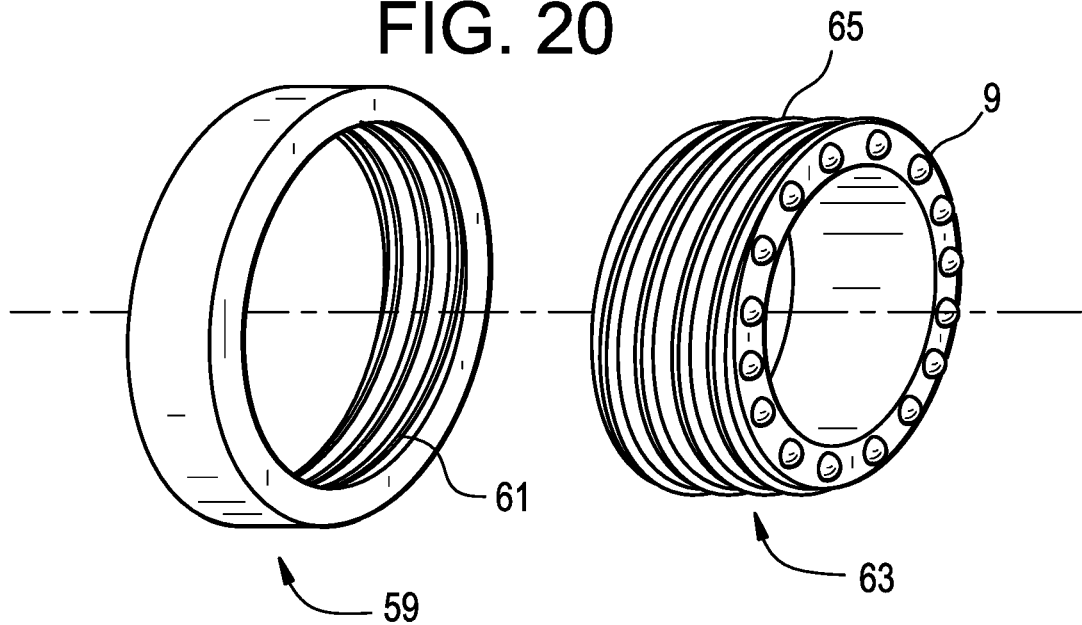
FIG. 20 discloses a two-piece LED-carrying tube forming a ledge.

In some embodiments, and now referring to FIG. 20, the tube component of the device can be provided in two parts: i) an outer annulus 59 having a threaded inner surface 61 and an outer diameter greater than the eye socket, and ii) an inner annulus 63 that carries the LEDs 9 and has a threaded outer surface 65 and an inner surface substantially equal to the diameter of the eye. In these embodiments, the inner annulus is threadably received in the outer annulus. Because the outer annulus has an outer diameter greater than the eye socket, it can not enter the eye socket so that the posterior face of the outer annulus acts as a ledge or stop against over-insertion of the LED-carrying inner annulus into the eye socket. Thus, during first use of the device, the user threadably selects the appropriate depth of reception and then keeps it there for the remainder of the treatments.

Figure 21:
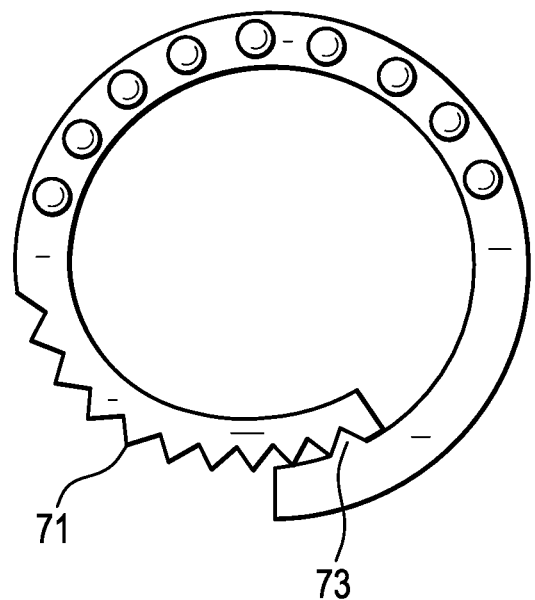
FIGS. 21-22 disclose a diameter-adjustable LED-carrying tube.
Figure 22:
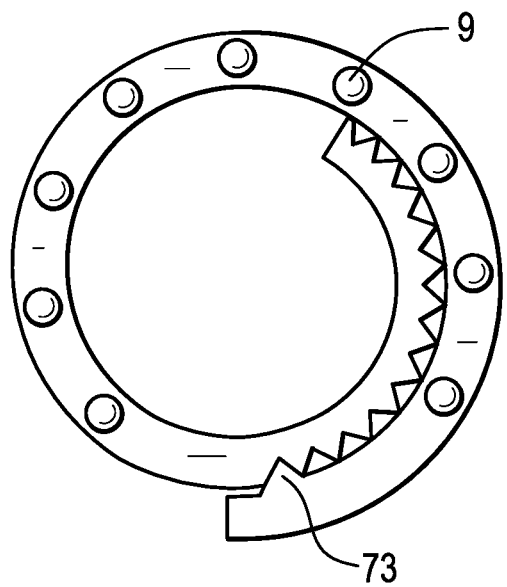

In some embodiments, and now referring to FIG. 21, the LED-carrying tube component of the device has an adjustable diameter. This feature allows the user to tailor the diameter of the tube so that it perfectly fits between the eye socket and eye of the user. In FIG. 21, the tube comprises a toothed coil having a first set of teeth 71 on the outer surface of a first end and a mating tooth 73 on the inner surface of the second end. If the user desires to reduce the diameter of the tube, and now referring to FIG. 22, the user squeezes the tube along the first set of teeth to release the mating, and then advance the first set of teeth partially past the mating tooth, and then release the first set of teeth, thereby reducing the diameter of the tube accordingly.

Figure 23:
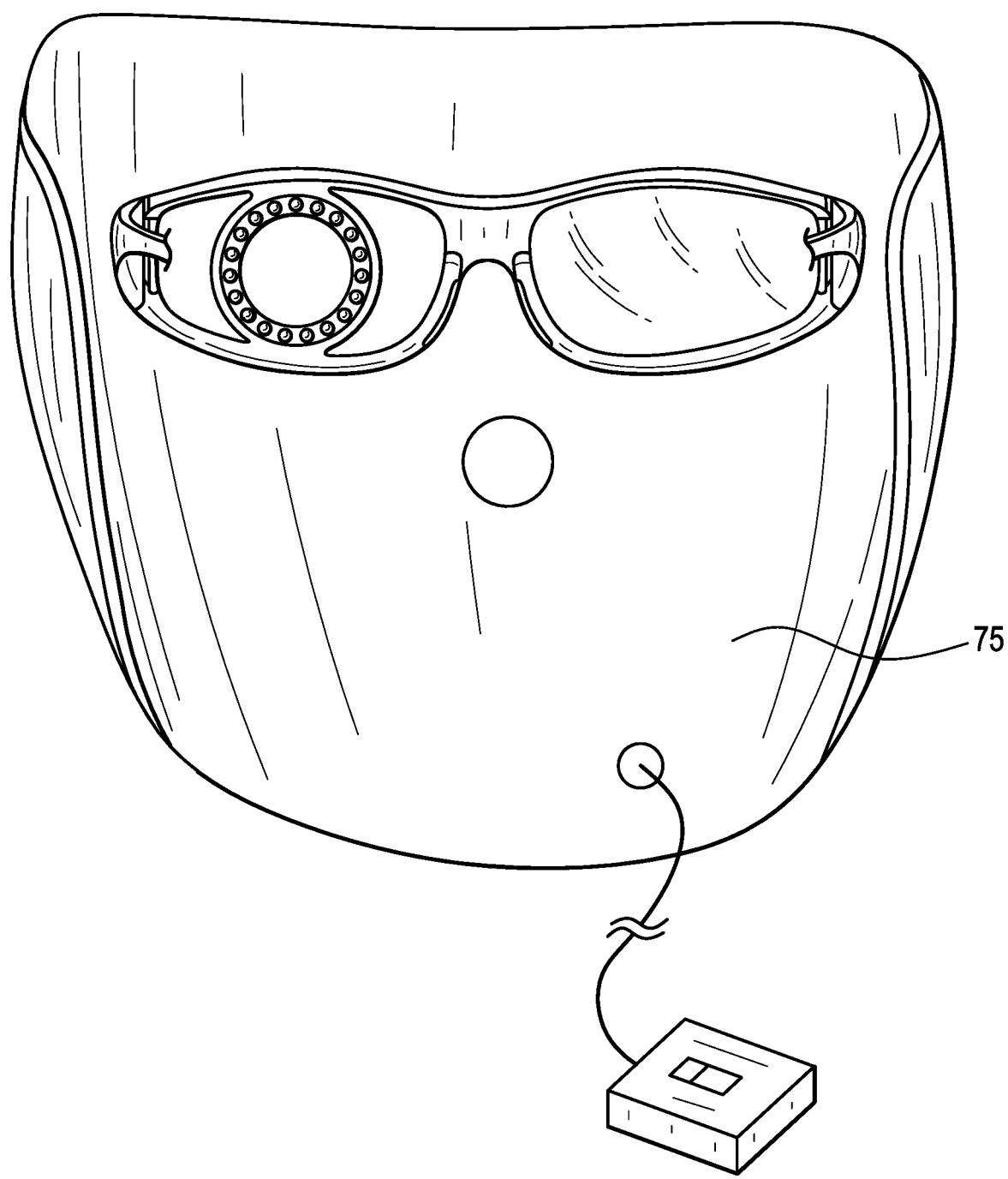
FIG. 23 discloses an LED-carrying eyeglass piece carried on a mask.

In some embodiments, and now referring to FIG. 23, the eyeglass and tube components are carried on a mask 75. The mask may present a more desirable facial appearance to some users than some of the devices presented herein. In some embodiments, a scent dispenser (such as a lavender dispenser) may be provided on the interior of the mask in order to dispense a calming scent to the user. Power may be provided to the mask, which can then be put in electrical connection with the eyeglass rims.

Figure 24:
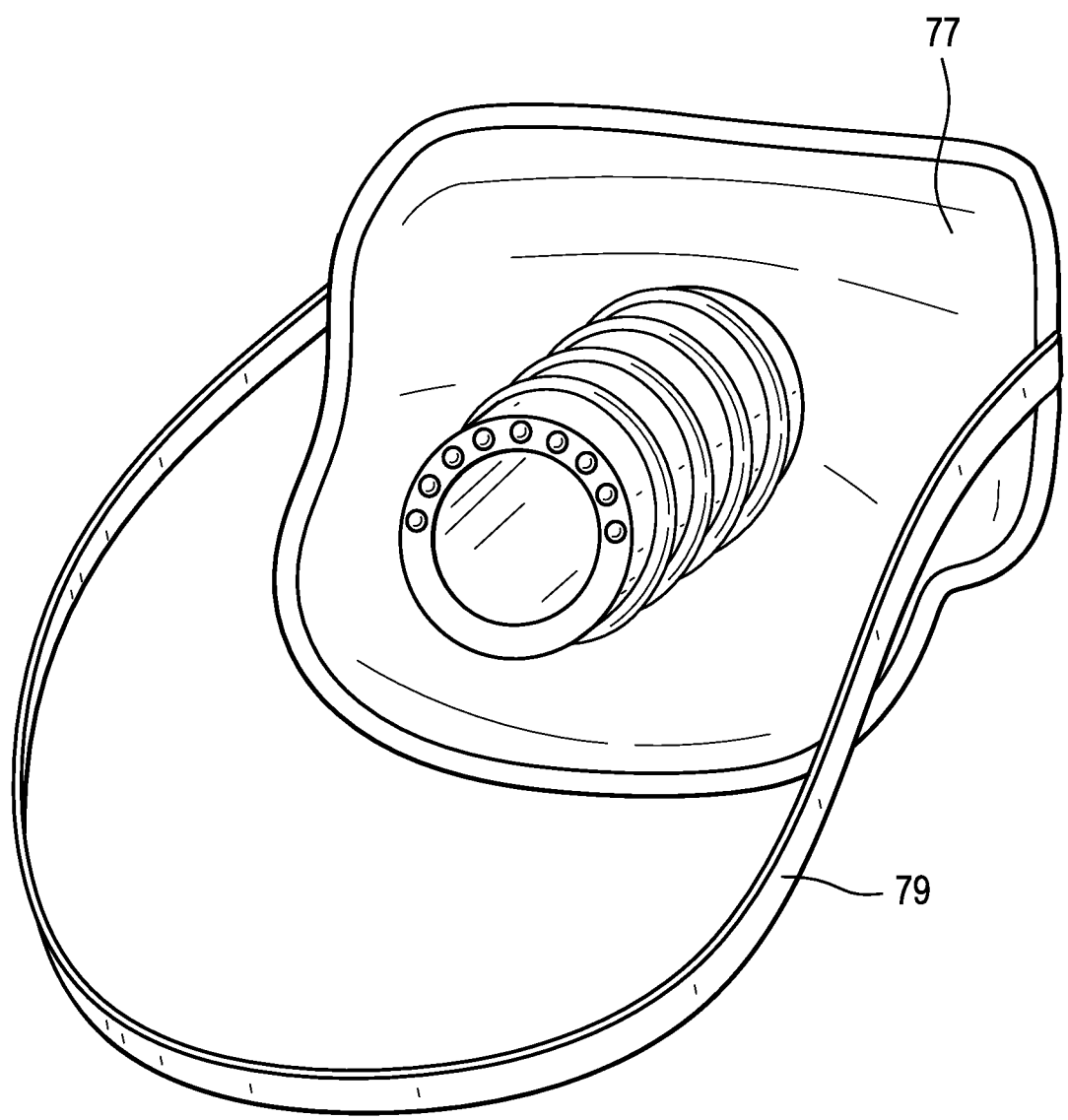
FIGS. 24-25 disclose LED-carrying tubes attached to eyepatchs.
Figure 25:
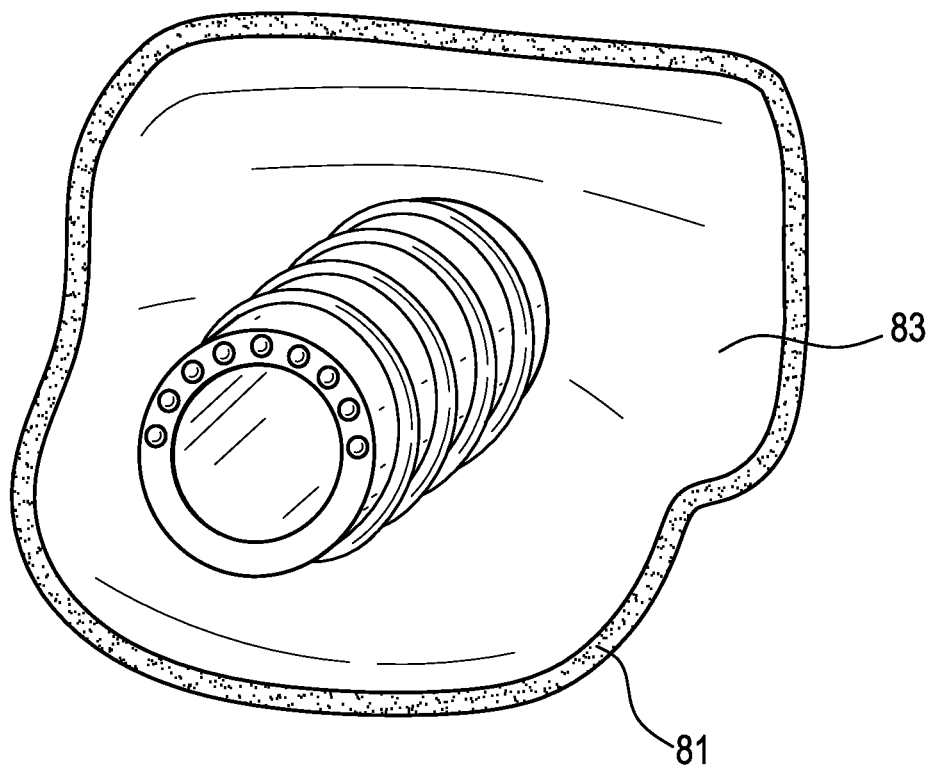

In some embodiments, and now referring to FIGS. 24-25, the LED-carrying tube or crescent component of the device is carried on an eye patch, and the LEDs are powered by energy accepted by the coil present on the radial surface of the tube. In FIG. 24, the eyepatch 77 is secured to the skull by a band 79. In some embodiments, the band is elastic. In other embodiments, the band is inelastic, but is adjustable in length. This adjustable length embodiment can be used to provide the appropriate amount of pressure of the tube upon the eyelid, thereby provided an acceptable compromise between tube insertion depth and comfort. In FIG. 25, the eyepatch is secured to the skull by an adhesive 81 that borders the perimeter of the patch 83.

Although the above FIGS. disclose devices that have a pair of rims and look somewhat like conventional eyeglasses, it is also contemplated that monocle-like devices can be suitably used to deliver therapeutic light as well.

In some embodiments, the devices are designed to be hand held. It is believed such devices might be useful in treatment embodiments in which the time of treatment is a few minutes (as opposed to 20-30 minutes).

In general such hand-held devices comprise:
a) a body portion having a power supply and a handle,
b) an intermediate portion having a first and second end, wherein the first end is attached to the body portion, and
c) a light-emitting portion attached to the second end of the intermediate portion,
wherein the light-emitting portion has a distal end adapted to emit light and shaped to fit between between the upper portion of the eye and the eye socket.

In one such embodiment, and now referring to FIG. 26, there is a hand-held device comprising:
a) a body portion 85 having a power supply (not shown),
b) an intermediate curved portion 87 having a first and second end, wherein the first end is attached to the body portion, and
c) a light-emitting portion 89 attached to the second end of the intermediate curved portion,
wherein the light-emitting portion has a distal end 91 adapted to emit light and shaped to fit between between the upper portion of the eye and the eye socket.

In some embodiments, the light-emitting portion is substantially circular, as in FIG. 26. In others, it is crescent-shaped 93 (as in FIG. 27).

In some embodiments, the light emitting portion comprises at least one red/NIR LED, preferably on its distal end portion. In others, the light emitting portion comprises a fiber fiber coupled to an NIR/red light LED that is located in a more proximal location of the device (such as the body portion).

Figure 28:
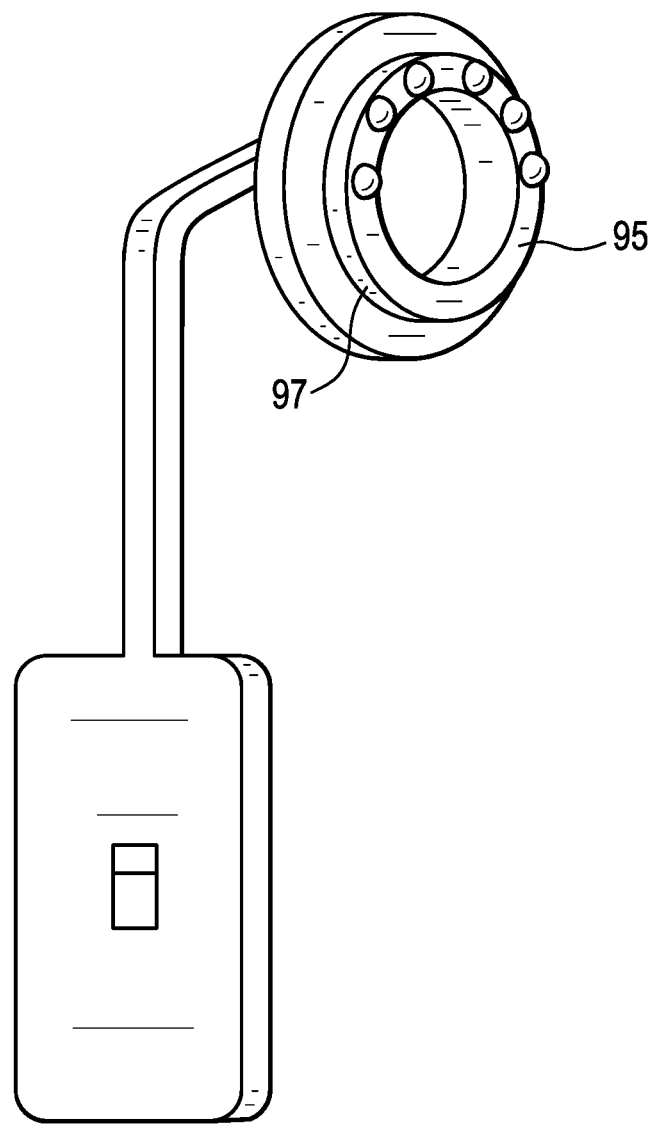
FIG. 28 discloses a handheld device with a LED-carrying tube forming a ledge.

In other embodiments of the hand-held devices, as in FIG. 28, the light-emitting portion has a tube component 95 having a ledge 97, wherein the outer diameter of the ledge is greater than the diameter of the eye socket such that light-emitting portion can not be overinserted into the eye socket space.

Figure 29:
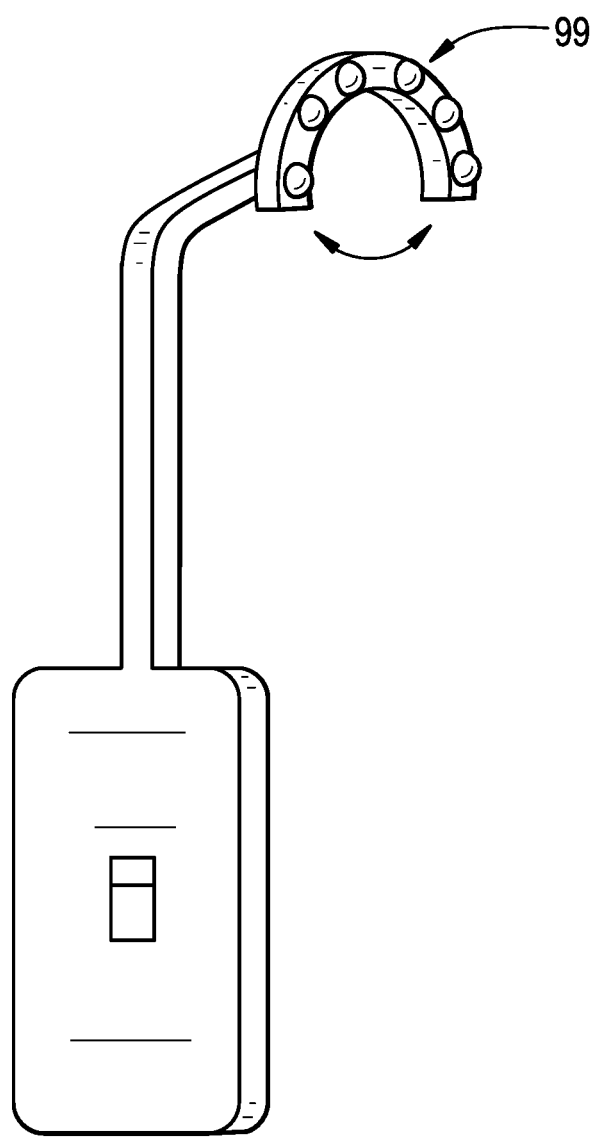
FIG. 29 discloses a handheld device with a LED-carrying crescent made of a shape memory material.

In some embodiments, as in FIG. 29, the light-emitting portion has a cresent shape 99 and is made of a shape memory material (such as a shape memory metal such as nitinol). The cresent is adapted to flex wide when under no load so as to accommodate large eyesockets. For smaller eyesockets, however, the crescent component flexes so as to be accepted into the smaller eye socket.

Figure 30:
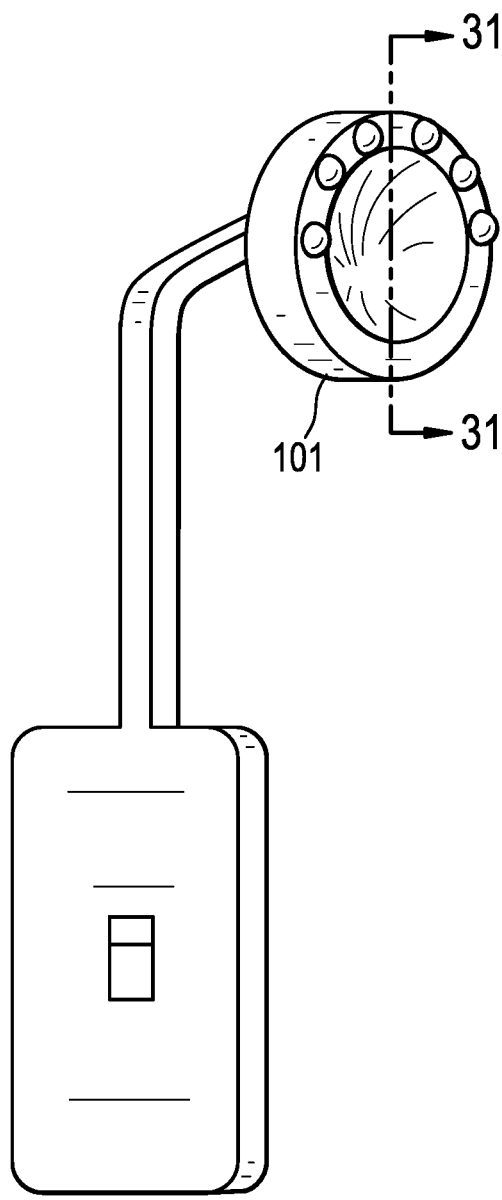
FIG. 30 discloses a handheld device with an LED-carrying distal end having a hemispherical recess therein.
Figure 31:
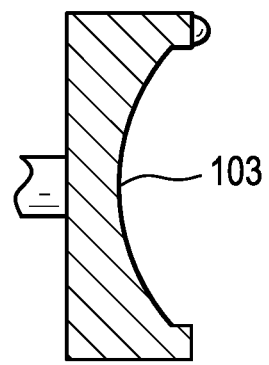
FIG. 31 discloses a cross-section of the distal end of FIG. 30.
Figure 32:
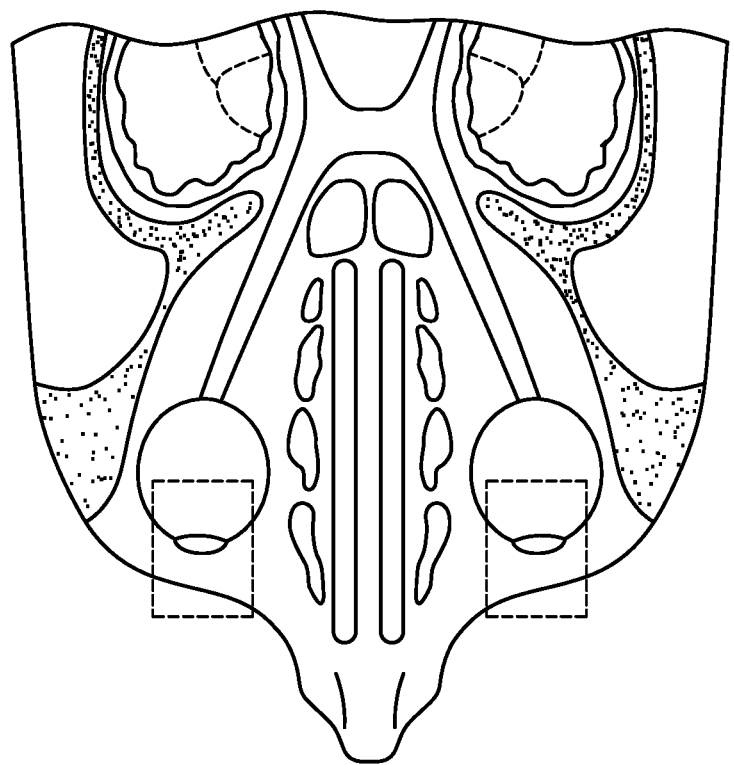
FIG. 32 is an axial cross-section of the human skull showing the proximity of the hippocampus to the inserted device.

In some embodiments, as in FIGS. 30-31, the light emitting portion carries LEDs on an outer ring and 101 has a hemispherically-shaped recess 103 within the ring. Preferably the recess is shaped to comfortably accommodate its placement against the eyelid of the user. In this embodiment, the surface of the recess acts as a stop against over insertion of the light-emitting portion in the eye socket.

In some embodiments, and now referring back to FIG. 9, a first portion of the LEDs (LED1) are carried on a distal end of the tube and a second portion of the LEDs (LED2) are carried on the radial outer surface of the tube. This allows for irradiation of OFC that is both above and posterior to the device.

Although many of the features disclosed above are disclosed in the context of a single embodiment (e.g., FIG. 29 discloses a shape memory crescent in the context of a hand-held device), it is clear that the general concepts disclosed herein are applicable to other disclosed embodiments as well. For example, the shape memory crescent is also applicable to crescents used in eyeglass-containing embodiments as well.

By way of example and not limitation, the following features may be provided on any of the embodiments disclosed herein:
a) bilateral delivery of red/NIR light over each eyelid, either simultaneously or sequentially,
b) threaded tubes and threaded rims,
c) a distal fiber optic coupled with a more proximal LED,
d) an actuator on the device,
e) a coil for coupling remote energy to power the device,
f) a visible light indicator that indicates the power is on,
g) a power supply provided on or within the device,
h) light emission from a component located on the radial portion of the device,
i) a flexible nose bridge,
j) an LED-carrying flange extending posteriorly from the rim,
k) rubber strips attached to the device providing an o-ring function,
l) a ratcheting feature for selective depth adjustment or selective diameter adjustment,
m) a ledge for providing a depth stop,
n) a mask for providing a better appearance,
o) an eyepatch,
p) a crescent shaped component for carrying the LEDs,
q) a crescent or tube made from a shape memory material,
r) an LED-carrying tube having an inner hemispherical recess for providing a depth stop.

In some embodiments, the proximity of the retina to the LEDs drives the selection of an irradiation dose known to be safe to the retina. In this respect, it is known that several clinicians have delivered doses of red/NIR light to the retina in a (largely successful) attempt to treat macular degeneration. See the review article of Geneva, *Int. J. Ophthalmol.*, 9(1) Jan. 18, 2016. For example, Tang treated diabetic macular oedema by delivering 670 NIR nm light through a closed eyelid to the retina at an intensity of about 300 mw/cm$^2$ for a duration of 80 seconds to produce a fluence of 25 J/cm$^2$. The treatment caused a beneficial reduction in focal retinal thickening in all the treated eyes. Tang, *Br. J. Ophthalmol.*, 2014, August, 98(8) 1013-15. Similarly, Merry reported treating macular degeneration by delivering 670 nm light to the retina at an intensity of 50-80 mw/cm$^2$ for 88 seconds to provide a fluence of 4-7.68 J/cm$^2$. Merry, "Treatment of dry Age-related Macular Degeneration with Photobiomodulation", presented at ARVO, Fort Lauderdale, Fla., May 7, 2012. Lastly, LumiThera recently presented on May 5, 2016 the successful results of its TORPA II study which used red, yellow and NIR multi-wavelength light on patients to treat Age-Related Macular Degeneration.

Therefore, in some safety-driven embodiments, red/NIR light is delivered from the device at a source intensity of about 300 mw/cm$^2$ for a duration of 80 seconds to produce a fluence of 25 J/cm$^2$. It is believed that these safety-driven embodiments provide sufficient fluence and intensity to beneficially treat the OFC, while at the same time providing a dose of light to the retina that is no more than the safe doses that have been clinically delivered to the retina in a deliberate fashion. In this regard, it is noted that the Gonzalez-Lima group reported delivering substantially this level of light transcranially to improve executive function in participants and patients. The Gonzalez-Lima group reported delivering NIR (1064 nm) light through the forehead to the prefrontal cortex at an intensity of about 250 mw/cm$^2$ for a duration of 240 seconds to provide a total fluence of about 60 J/cm$^2$. Blanco, *J. Neuropsychol.*, Nov. 28, 2016. The 250 mw/cm$^2$ intensity and 60 J/cm$^2$ fluence values were also selected by the Hamblin group who treated depression in Schiffer, *Behav. and Brain Functions*, 2009, 5, 46-58. Just as the Gonzalez-Lima/Hamblin efforts found beneficial results in irradiating the forehead (and thus the prefrontal cortex) with this quality and quantity of light, it is believed that the devices herein situated in the space between the upper eye and the eye socket will operate likewise for the OFC.

In a further safety-driven effort, in embodiments having LEDs situated on the radial surface of the tube/crescent, the corresponding inner surface is lined with a reflective coating to shield the retina from any reflected LED light. Similarly, the inner surface of the distal end portion of the tube can comprise a reflective coating.

Without wishing to be tied to a theory it is believed that red or infrared light induces synaptic plasticity in the areas of the brain that are under distress, disordered or damaged, but leaves normal regions unaffected. This enhanced plasticity leads not only to a beneficial local increase in the cortical volume, but also to a beneficial functional reorganization in the network of the affected area.

There have been numerous studies reporting the beneficial effect of transcranial NIR light upon depressed patients: Schiffer, *Behav. Brain Funct.*, 2009 Dec. 8; 5:46 reported the psychological benefits 2 and 4 weeks after a single treatment with near infrared light to the forehead in a pilot study of 10 patients with major depression and anxiety. P. Cassano et al., *Psychiatry J.* 2015, 352979 (2015) reported on a proof of concept study for near-infrared transcranial radiation for major depressive disorder in which 2 of the 4 treatment completers demonstrated remission. M. A. Naeser et al., *J. Neurotrauma* 31(11), 1008-1017 (2014) reported significant improvements in cognitive performance after transcranial and intranasal red/near-infrared light-emitting diode treatments in chronic, mild traumatic brain injury, in which three subjects (37%) showed antidepressant response (decrease of BDI-II total score ≥50% from baseline) after 6 weeks of PBM treatment (mean BDI-II total scores were 14.8 6.5 SD). Two of them maintained the antidepressant response after 8 additional weeks of follow-up.

It has been reported in the literature that red/near infra-red light saves neurons that have been challenged by neurotoxics from apoptosis. In particular, Wong-Riley, *J Biol Chem.* 2005 Feb. 11; 280(6):4761-71. reports that irradiating neurons with 670 nm red light significantly reduced neuronal cell death induced by 300 mM KCN from 83.6% to 43.5%.

The general concept of repairing brain cells through red/NIR light irradiation is also well supported by the literature. Wollman, *Neurol. Res.* 1998, July 20(5) 470-2 reports that providing daily 3.6 J/cm$^2$ doses of red light from a He—Ne laser to cortex explants resulting in caused a significant amount of sprouting of cellular processes outgrowth. Wollman concludes that the irradiation induces neurite processes sprouting and improves nerve tissue recovery. Similarly, Wollman, *Neurol. Res.* 1996 Oct. 18(5) 467-70 reports the enhanced migration and massive neurite sprouting of cultured rat embryonal brain cells subject to an 8 minute dose of a 0.3 mW, He—Ne laser. Therefore, the red/NIR light of the present invention may further cause repair and regeneration of damaged neuronal cells.

Without wishing to be tied to a theory, it is believed that the therapeutic neuroprotective and neuroregenerative effects of red/NIR light described above may also be due to a) an increase in ATP production in the irradiated neurons, and b) an increase in the activity of local anti-oxidant enzymes superoxide dismutase (SOD) and catalase.

It is believed that irradiating neurons in the brain with red light will likely increase ATP production from those neurons. Mochizuki-Oda, *Neurosci. Lett.* 323 (2002) 208-210, examined the effect of infrared light on energy metabolism in the rat brain and found that irradiating neurons with 4.8 W/cm$^2$ of 830 nm infrared light increased ATP production in those neurons by about 19%.

Without wishing to be tied to a theory, it is further believed that the irradiation-induced increase in ATP production in neuronal cell may be due to an upregulation of cytochrome oxidase activity in those cells. Cytochrome oxidase (also known as complex IV) is a major photoacceptor in the human brain. According to Wong-Riley, *Neuroreport*, 12:3033-3037, 2001, in vivo, light close to and in the near-infrared range is primarily absorbed by only two compounds in the mammalian brain, cytochrome oxidase and hemoglobin. Cytochrome oxidase is an important energy-generating enzyme critical for the proper functioning of neurons. The level of energy metabolism in neurons is closely coupled to their functional ability, and cytochrome oxidase has proven to be a sensitive and reliable marker of neuronal activity.

By increasing the energetic activity of cytochrome oxidase, the energy level associated with neuronal metabolism may be beneficially increased. Indeed, the literature reports that NIR/red light reverses the inhibitory effects of neurotoxins upon cytochrome oxidase activity, leading to increased energy metabolism in neurons functionally inactivated by toxins. Wong-Riley *Neuroreport* 12(14) 2001: 3033-3037 and Wong-Riley, *J. Biol. Chem*, supra.

According to Kamanli, *Cell Biochem. Func.* 2004, 22:53-57, catalase detoxifies hydrogen peroxide and converts lipid hydroperoxides into non-toxic alcohols, and is essential for the inhibition of inflammation related to the function of neutrophils. Romm, *Biull. Eksp. Biol. Med.* 1986 October 102(10) 426-8 reports that laser irradiation of wounds results in a decreased chemiluminescence that is attributable to activation of catalase in the tissue fluid.

Therefore, it is believed that irradiating an affected brain with an effective amount of NIR/red light will therapeutically increase of the activity of catalase in the irradiated region, thereby attenuating the deleterious effect of hydrogen peroxide upon the neurons in the affected brain. According to Kamanli, supra, SOD catalyses dismutation of the superoxide anion into hydrogen peroxide. The literature repeatedly reports that red/NIR light irradiation of inactivated SOD increases its activity. For example, Vladimirov, *Biochemistry (Moscow)* 69(1) 2004, 81-90 provides a review including the photoreactivation of Cu—Zn SOD under He—Ne laser. Karu, *Laser Ther.* 1993, 5, 103-9 reports that reactive oxygen species in human blood were found to be suppressed after laser diode illumination at 660 nm, 820 nm, 880 nm and 950 nm. This affect has been attributed by other authors to the activation of SOD or catalase. Volotovskaia *Vopr Kurortol Zizioter Lech Fiz Kult* 2003 May-June (3)22-5 reports that 632 nm He—Ne laser irradiation of blood has an anti-oxidant effect as shown by activation of SOD. Ostrakhovich Vestn Ross Akad Med Nauk. 2001(5) 23-7 reports that infrared pulse laser therapy of RA patients caused an increase in SOD activity. Gorbatenkova Biofizika, 1988 July-August 33(4) 717-9 reports that SOD that was inactivated by hydrogen peroxide was reactivated by a 450-680 nm red light laser. Vladimirov, *Free Rad. Biol. Med.* 1988, 5(5-6) 281-6 reports the inactivation of SOD by its incubation in a low pH 5.9 solution and its subsequent reactivation by helium-neon laser light. Catalase was found to be reactivated as well. Cho, *In Vivo*, 2004, September-October 18(5) 585-91 reports on the use of low level laser therapy (LLLT) to treat knee joints that have been induced with OA by injection of hydrogen peroxide. SOD was reported to increase about 40% in the OA group as compared to controls.

Therefore, it is believed that irradiating the affected brain with an effective amount of red/NIR light will therapeutically increase of the activity of SOD in the irradiated region, thereby attenuating the deleterious effect of superoxide anion upon the neurons in the distressed brain.

According to Leung, *Laser Surg. Med.* 31:283-288 (2002), nitric oxide enhances oxidative insult by reacting with superoxide anion to form a stronger oxidant, peroxynitrite, which leads to mitochondrial dysfunction, DNA damage and apoptosis. Leung, supra, investigated the effect of low energy red laser after stroke in rats, and found that red light can suppress NO synthase activity. In particular, Leung found that irradiating a portion of the rat's brain with a 660 nm red light (average power 8.8 mW, 2.64 J/cm$^2$) reduced NOS activity up to about 80% over that in unirradiated stroke rats, and up to about 60% over the NOS activity in normal rats. Leung concluded that low energy laser may be protective by suppressing the activity of NOS.

Without wishing to be theory, it is believed that irradiation of a portion of a distressed brain will similarly therapeutically suppress NO synthase activity, thereby attenuating peroxynitrite activity.

It is noted that Leung, supra, also reported that red/NIR light irradiation of the brain resulted in a TGF-β tissue concentration of 1-6 ng/ug protein of tissue. Thus, red light irradiation of the OFC may very well be an attractive non-invasive way of generating large amounts of TGF-β within the brain.

Moreover, the literature has reported other highly beneficial effects of red light, including its attenuation of the immune response following neuronal injury. Byrnes, *Lasers Surg. Medicine* 9999:1-15(2005) reports that 810 nm light promotes the regeneration and functional recovery of the injured spinal cord, and significantly suppressed IL-6 and iNOS expression and immune cell activation. Of note, Byrnes reports a 171-fold decrease in IL-6 expression and an 80% reduction in iNOS expression when the spinal cord lesion was irradiated on a daily basis with about 100 J/cm$^2$ red light for about 2 weeks.

Therefore, in light of the above studies, and without wishing to be tied to a theory, it is believed that the decreased cortical volume and disorder of the anterolateral OFC play a role in the depressed state of the PND mother. It is further believed that these deficits can be reversed by low level laser therapy ("LLLT") treatment of these regions with red/near infrared light ("red/NIR light"). In particular, it is believed that red/NIR light will beneficially act upon the OFC through the following avenues:

a) increasing the amount of ATP;
b) increasing the amount of BDNF;
c) increasing the amount of bcl-2, and
d) increasing the amount of sprouting, leading to network reorganization.

Oron, *Photomed Laser Surg.* 2007 June; 25(3):180-2. (2007) reports that in vitro red/NIR light approximately doubles the amount of ATP in neurons. Since metabolic processes of the brain substantially use ATP as their fuel, it is believed that the increase in ATP afforded by LLLT will help normalize the OFC.

Zhang *Cell Physiol Biochem* 2008; 22(1-4):215-22 reports that LLLT activates PKC in neurons within one hour of the irradiation (Zhang, 2008). Because it is known that PKC increases serotonin release from synapse (*Psychopharmacology (Berl)*. 1989; 99(2): 213-8.) and PKC has been implicated in mediating neuronal plasticity, and that increasing the availability of serotonin provides a positive benefit for depressed patients, the activation of PKC should provide a therapeutic benefit to the depressed patient.

As discussed above, it is now believed that the effectiveness of many conventional antidepression treatments may lie in their ability to induce neurotrophins such as brain-derived neurotrophic factor (BDNF), in the patient's brain. It has been shown that LLLT acts upon neurons to increase BDNF 5× in neurons (Byrnes Lasers Surg Med. 2005 August; 37(2):161-71.), and (Anders IEEE J. Quantum Electronics, 14/1 January/Februrary 2008, 118-125). The 5×BDNF induction produced by LLLT compares favorably with the increase in BDNF induced by antidepressants, and is approximately the same level of BDNF induction generated by ECT.

bcl-2 is an anti-apoptotic gene that has been implicated in mediating neuronal plasticity. Manji, *Psychopharmacol Bull* 2001 Spring; 35(2):5-49 and Manji, *Am J Psychiatry*. 2005 April; 162(4):805-7 report that bcl-2 expression correlates with clinical benefit of antidepressants. In this respect, red light has been shown to increase bcl-2 in neurons (Liang, *Neuroscience*. 2006 May 12; 139(2):639-49,) and (Zhang, supra, 2008)

Further without wishing to be tied to a theory, it is further believed that red/NIR light therapy of the OFC will provide a number of advantages to the patient.

First, red/NIR light therapy is a completely non-toxic therapy. Thus, it appears that its use poses no known danger to the patient. Therefore, red/NIR light therapy/LLLT can be used by a nursing mother without any apparent risk to the child.

Second, it is believed that red/NIR light therapy will work much more quickly than conventional antidepressants, with LLLT providing a first round of benefit within about an hour of the initial irradiation and a second round of benefit within a few days of the initial irradiation.

Respecting highly acute events, Oron (supra, 2007) reports that in vitro red/NIR light increases ATP in neurons within 10 minutes of the application of red/NIR exposure, while Zhang reports that LLLT activates PKC in neurons within one hour of the irradiation (Zhang, supra, 2008). Thus, two mechanisms are acting favorably upon the patient within an hour of LLLT treatment.

Respecting more subchronic events, Anders, 2008 reports that red/NIR light increases BDNF in neurons within 3-7 days of the beginning of red/NIR light exposure. Zhang (2008)/Liang & Whelan (2006) report that red/NIR light increases bcl-2 in neurons within 6-28 hours respectively of the beginning of red/NIR light exposure. In contrast, Wada 2005 reports that only chronic use of lithium upregulates bcl-2 expression (Wada, *J Pharmacol Sci.* 2005 December; 99(4):307-21.) and only chronic lithium correlates with clinical benefits (Wada 2005)

Further evidence of the quick acting nature of red light is found in studies examining the effect of red light upon neuronal sprouting. Wollman, *Neurol. Res.,* 1998, 20: 470-2 reported that human cortical explants exposed to red/NIR light displayed significantly increased sprouting after only 6 days. Also, Rochkind, *Lasers Surg. Med.* 41, 277-281 (2009) reported that 780 nm light irradiation of embryonic rat brain cultures induced rapid sprouting of nerve processes within 24 hours and a 3-fold increase in large perikaryae after 4 days. Rochkind reported that this "precocious appearance of large neurons is unlike the usual growth pattern in which neurons grow and become large only after several weeks in culture." Rochkind found that irradiation at 50 mW for one minute induced the most significant change. Therefore, because of the red/NIR light irradiation-induced induction of early sprouting, it is believed that the NIR/red light device of the present invention may be able to provide a clinical benefit to the patient within a few days of beginning treatment.

The present inventor are aware of at least two reports of very favorable effects of red/NIR light irradiation of neuronal cells at fluences (doses) of less than 1 J/cm$^2$. As discussed above, Byrnes, *Lasers Surg Med.* 2005 August; 37(2):161-71 found a significant (P<0.05) increase in brain derived neurotrophic factor (BDNF) and glial derived neurotrophic factor (GDNF) in the 0.2 J/cm$^2$ group in comparison to the non-irradiated group. Oron, *Photomed Laser Surg.* 2007 June; 25(3):180-2 reports that normal human neural progenitor (NHNP) cells were grown in tissue culture and were treated by Ga—As laser (808 nm, 50 mW/cm$^2$, 0.05 J/cm$^2$). They found that the quantity of ATP in laser-treated cells 10 minutes after laser application was 7513+/−970 units, which was significantly higher (p<0.05) than the non-treated cells, which comprised 3808+/−539 ATP units. In sum, Oron found that the neuronal ATP level was essentially doubled by infrared LLLT. In addition, Byrnes, *Lasers Surgery Medicine*, March 2005, 36(3) 171-85 reports that dosages as low as 0.001 J/cm$^2$ stimulate cellular activity (such as DNA, RNA and protein production, proliferation and motility). Therefore, it is believed that fluences as low as about 0.01 J/cm$^2$ (and possibly even about 0.001 J/cm$^2$) will be effective in providing therapy to the pertinent neurons of the perinatal depression (PND) patient.

In some embodiments, the light source is situated to produce about 1-90 milliwatt/cm$^2$, and preferably 7-25 milliwatt/cm$^2$ of irradiation upon the cortical surface.

In accordance with US Patent Publication 2004-0215293 (Eells), LLLT suitable for the neuronal therapy of the present invention preferably has a wavelength between 630-1000 nm and power intensity between 25-50 mW/cm$^2$ and is provided for a time of 1-3 minutes (equivalent to an energy density of 2-10 J/cm$^2$). Eells teaches that prior studies have suggested that biostimulation occurs at energy densities between 0.5 and 20 J/cm$^2$. Wong-Riley. *J. Biol. Chem.* 2005 Feb. 11, 280(6), 4761-71 reports that fluences as high as 30 J/cm$^2$ appear to be effective in preventing cell death in neurons exposed to the mitochondrial poison KCN. In some embodiments, the preferable energy density of the present invention is between 0.1 and about 30 J/cm$^2$, more preferably between 0.5-20 J/cm$^2$, most preferably between 2-10 J/cm$^2$. In summary, a preferred form of the present invention uses red and near infrared (red/NIR) wavelengths of 630-1000, most preferably, 670-900 nm (bandwidth of 25-35 nm) with an energy density fluence of 0.5-20 J/cm$^2$, most preferably 2-10 J/cm$^2$, to produce photobiomodulation. This is accomplished by applying a target dose of 1-90 mW/cm$^2$, preferably 25-50 mW/cm$^2$ LED-generated light for the time required to produce that energy density.

It is further believed that red/NIR light irradiation of neurons will produce a significant upregulation in brain derived neurotrophic factor (BDNF) and glial derived neurotrophic factor (GDNF). Byrnes, *Lasers Surg Med.* 2005 August; 37(2):161-71 reports that olfactory ensheathing OECs were purified from adult rat olfactory bulbs and exposed to 810 nm light (150 mW; 0, 0.2, or 68 J/cm$^2$). Byrnes found that a significant (P<0.05) increase in BDNF, GDNF and collagen expression in the 0.2 J/cm$^2$ group in comparison to the non-irradiated and high dose groups.

Of note, it has been reported that the neuroprotective effects of red/NIR light can be effected by a single irradiation on the order of minutes. Wong-Riley, *J. Biol. Chem.* 2004, e-pub November 22, reports that irradiating neurons with 670 nm red light for only ten minutes results in neuroprotection. Similarly, Wong-Riley *Neuroreport* 12(14) 2001:3033-3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme".

In some embodiments, the red/NIR light irradiation is delivered in a continuous manner. In others, the red/NIR light irradiation is pulsed (usually between 1 and 10 Hz) in order to reduce the heat associated with the irradiation. Without wishing to be tied to a theory, it is believed that pulsed light may be more effective in achieving the vibratory oscillation of the catalase and SOD molecules.

Wavelength

Preferably, the light of the present invention has a wavelength of between about 600 nm and about 1100 nm. In some embodiments, the wavelength of light is between 800 and 900 nm, more preferably between 800 nm and 860 nm. In this range, red/NIR light has not only a large penetration depth (thereby facilitating its transfer to the fiber optic and SN), but Wong-Riley reports that cytochrome oxidase activity is significantly increased at 830 nm, and Mochizuki-Oda reported increased ATP production via a 830 mn laser. In some embodiments, the wavelength of light is between 600 and 700 nm. In this range, Wong-Riley reports that cytochrome oxidase activity was significantly increased at 670 nm. Wollman reports neuroregenerative effects with a 632 nm He—Ne laser.

Penetration Depth

Respecting penetration depths, Byrnes, *Lasers Surg. Medicine* 9999:1-15 (2005) reports that an effective amount of 810 nm light was able to traverse a 1 cm thick rat spinal cord. The penetration depths of various wavelengths of red light in grey matter brain tissue have been reported in Yaroslaysky, *Phys. Med. Biol.* 47 (2002) 2059-73 as follows:

| Wavelength | Penetration Depth (mm) |
| --- | --- |
| 630 nm | 0.83-4.06 |
| 675 nm | 1.29 |
| 670 nm | 4.4 |
| 1064 nm | 1.18-3.28 |

In general, the literature has reported that infrared light provided deeper penetration into brain tissue than red light. Tedford, *Lasers in Surgery and Medicine* 47:312-322 (2015). Therefore, in preferred embodiments, infrared light is used. Tedford further reports that infrared light attenuates in brain tissue at a rate of about 10 fold per centimeter.

Fluence

In some embodiments, the light source is situated and applied to irradiate brain tissue with between about 0.02 $J/cm^2$ and 200 $J/cm^2$ energy. Without wishing to be tied to a theory, it is believed that light transmission in this energy range will be sufficient to increase the activity of the cytochrome oxidase and anti-oxidant activity around and in the neurons. In some embodiments, the light source is situated to irradiate target tissue with more than 10 $J/cm^2$, and preferably about 100 $J/cm^2$ energy. In some embodiments, the light source is situated to irradiate adjacent tissue with between about 0.2 $J/cm^2$ and 50 $J/cm^2$ energy, more preferably between about 1 $J/cm^2$ and 10 $J/cm^2$ energy.

Intensity

In some embodiments, the light source is situated to produce an energy intensity of between 0.1 watts/$cm^2$ and 10 watts/$cm^2$. In some embodiments, the light source is situated to produce about 1 milliwatt/$cm^2$.

Power

In some embodiments, the infrared LED irradiates with a power of at least 0.5 watts, more preferably at least 0.7 watts, more preferably at least 1 watt. In some embodiments, the infrared LED has a power of at least 3 watts, more preferably at least about 5 watts. In some embodiments, this high power LED is the SLTMAKS 10 PCs/lot High power LED Chip 740 nm 850 nm IR LED 3 W 5 W Emitter Light Lamp LED Beads for LED Grow Light at aliexpress. Another high power 3 W 850 nm LED is available from Ledguhon at aliexpress. Another is the 10 Pcs Hontiey 3 W 850 nm LED Bo6XQDWQZT at amazon.

Target Structures

It is believed that brain structures that can be beneficially irradiated with the device of the present invention include the lateral OFC. These structures have been implicated as neural correlates of depression.

Timing

Of note, it has been reported that the neuroprotective effects of red light can be effected by a single irradiation on the order of minutes. Wong-Riley, *J. Biol. Chem.* 2004, supra, reports that irradiating neurons with 670 nm red light for only ten minutes results in neuroprotection. Similarly, Wong-Riley *Neuroreport* 12(14) 2001:3033-3037 reports that a mere 80 second dose of red light irradiation of neuron provided sustained levels of cytochrome oxidase activity in those neurons over a 24 hour period. Wong-Riley hypothesizes that this phenomenon occurs because "a cascade of events must have been initiated by the high initial absorption of light by the enzyme".

Therefore, in some embodiments of the present invention, the therapeutic dose of red light is provided on approximately a daily basis, preferably no more than 3 times a day, more preferably no more than twice a day, more preferably once a day.

Continuous/Pulsed

In some embodiments, the red/NIR light irradiation is delivered in a continuous manner. In others, the red/NIR light irradiation is pulsed in order to reduce the heat associated with the irradiation. Without wishing to be tied to a theory, it is believed that pulsed light may be more effective in achieving the vibratory oscillation of the catalase and SOD molecules.

In some embodiments, the LED devices comprises electronics adapted to provide a substantially constant current.

Applications

It is believed that the above devices are useful in treating brain disorders involving the orbitofrontal cortex, including traumatic brain injury, chronic traumatic encephalopathy, concussion, Alzheimer's Disease, depression, postpartum depression, hydrocephalus, frontotemporal dementia, and stroke involving the anterior cerebral artery.

Lithium

As lithium's beneficial action upon patients with bipolar disorder and schizophrenia is also thought to be due to its ability to enhance neuroplasticity and reorganization, it is believed that the dose of lithium (which has certain unwanted side effects) given to these patients can be reduced by concomitant administration of lithium and red/infrared light. Therefore, there is provided a method of treating a patient with a brain disorder (preferably bipolar disorder or schizophrenia) comprising the steps of:

a) administering an effective amount of lithium to the patient, and b) irradiating the patient's brain with an effective amount of infrared or red light, wherein the effective amount of lithium administered is less than the dose required to treat the patient in the absence of red/infrared light administration.

Behaviour

In addition, simultaneous use of red/NIR light therapy with established behavior change interventions such as meditation, exposure therapy, cognitive behavioral therapy, and guided imagery can enhance the efficacy of those treatments.

A related approach for enhancing adherence purely for the stimulation of the brain is to use the Premack Principle. The Premack Principle states: If behavior B is of higher probability than behavior A, then behavior A can be made more probable by making behavior B contingent upon it. This is also known as "relativity theory of reinforcement", based on the work of David Premack. As one example, if a person routinely drinks a cup of coffee, we would make that behavior incumbent on first using the red light therapy. Behaviors can also be simultaneously paired together in some cases e.g., use the device while reading the morning paper (e.g., "If you don't use the device, you don't get to read the paper").

It is contemplated to use red/NIR light in conjunction with exposure therapy for fears, phobias and traumas. There are three ways to expose clients to their fears during systematic desensitization. First, exposure to fears can be accomplished through mental imagery. This approach can be more convenient and allows patients to complete treatment without ever leaving their therapist's office. Second, in vivo (direct exposure to the feared stimulus) is also possible. This option can be more complex (e.g., going to a dental office to provide exposure for a patient with a dental phobia), but appears to produce outcomes superior to imaginal exposure. Third, computer simulation (virtual reality) has been successfully used as a means of exposing a patient to feared stimuli. Simultaneous use of red/NIR light during these exposures might enhance the efficacy/benefit of the treatment.

Uses

Professional use of these devices could include:

a) First Responders EMS—This could be part of every head injury assessment and treatment could begin immediately while the patient is being transported to the trauma center;

b) Military Battlefield—Much like the role of the EMS, first responders, this could be part of a field medic, special forces units, MASH units, and larger base hospitals, and c) Sports Trainers, Coaches—Administration could begin immediately on the field after players sustain a concussion. This could be therapeutic and preventative for Chronic Traumatic Encephalopathy.

Consumer and self-administered uses of these devices could include:

a) Post-Partum Depression—Newly discharged mothers would use this in the peri-partum period, provided it was attractively packaged and marketed;

b) Antenatal depression— c) Alzheimer's Disease Benign Senile Forgetfulness—Senior citizens could administer treatments themselves or have in home care givers provide assistance for therapy. Venues would include assisted living and skilled nursing facilities;

d) Post Concussive Syndrome—Children and adolescents would benefit from therapy as many struggle with executive function tasks (math and reading) as they recover from sports related concussions. This has vast society implications;

e) First Aid Kits—Devices could be part of every First Aid kit for car, traveling, camping, home use, etc;

f) Acute Sports Injury|Concussion—Apart from the physical "contact" sports such as football, there potentially is a role for all sports including hiking, diving, particularly outdoorsman that are remote and not near medical care.

g) Obesity (wherein the gyms rectus is beneficially irradiated), h) Major depression i) Traumatic Brain Injury j) Obsessive-Compulsive Disorder k) Anxiety, and l) CTE.

FIG. 33

(Anatomy)

Moreover, since red light experiences high diffraction as it proceeds through soft tissue, it is possible for the entire lower portion of the prefrontal cortex to be irradiated with red light.

Therefore, in accordance with the present invention, there is provided a method comprising the steps of:

a) providing an device having a NIR/red light emitter,
b) positioning the emitter within the eye socket, and
c) activating the light source to irradiate brain tissue with an effective amount of NIR/red light.

(PPD

As discussed in US Published Patent Application US2011-0319878 (Codman II), PPD investigators have recently presented a number of functional MRI studies (fMRI) that examined maternal responses in healthy mothers to their own infants' pictures or sounds (crying or laughter). In general, the investigators found differential activation of a number of regions present in the lower anterior portion of the brain, including the medial and lateral orbitofrontal cortex (OFC), the temporal pole and the amygdala. See FIG. 33. These papers are reported below:

Noriuchi, *Biol. Psychitary* (2007), performed fMRI on 13 mothers viewing video clips of their own and other infants who demonstrated different attachment behaviours such as smiling at the infant's mother and crying for her. Noriuchi found that the orbitofrontal cortex (OFC) was specifically involved in the recognition of the mother's own infant. Noriuchi further found that the left OFC was associated with the joyful and happy response of the mother to her own infant while the right OFC was associated with the anxiousness of the mother.

Nitschke, *NeuroImage* 21 (2004) 583-592 reported on fMRIs of healthy mothers viewing photos of their infants and other infants, and reported that the mothers experience bilateral activation of the OFC when viewing their own infants, and that OFC activation correlated positively with pleasant mood ratings. Nitschke concluded that the data "implicate the orbitofrontal cortex in a mother's affective responses to her infant, a form of positive emotion . . . ."

Bartels, NeuroImage 21 (2004) 1155-1166 used fMRI to measure brain activity in mothers while they viewed pictures of their own and acquainted children, and found activity in the OFC.

Lenzi, *Cereb. Cortex*, 2008 Oct. 10, examined 16 mothers undergoing fMRI while observing and imitating faces of the own and others' children, and found that joy expressions evoked a response mainly in the right limbic and temporal pole areas, while ambiguous expressions elicited a response in the left high order cognitive and motor areas.

Ranote, *Neuroreport*, 2004 Aug. 6; 15(11) 1825-9, reported the neural correlates of maternal responsiveness shown by healthy mothers viewing alternating video of their own infant, an unknown infant and a neutral video. Ranote reported finding signal change in the bilateral OFC, amygdala and temporal pole, and concluded that the amygdala and temporal pole may be key sites in mediating a mother's response to her infant.

Minagawa-Kawai, *Cerebral Cortex*, February 2009, 19, 284-292, reported that mothers viewing their own child versus unfamiliar infants elicited increased activations around the anterior part of the OFC.

Leibenluft, Biol. Psychiatry, 2004, 56, 225-232, investigated the neural response of (healthy) mothers viewing their own child versus a familiar child, and found activation in the amygdala, insula, anterior paracingulate cortex, posterior superior temporal sulcus Other studies have examined adult responses to stimuli from unfamiliar infants, and found activations in the amygdala and OFC. For example, Kringelbach, *PLoS ONE*. 2008 Feb. 27; 3(2):e1664, investigated whether adults show specific brain responses to unfamiliar infant faces (as compared to adult faces), and found that highly specific brain activity occurred in the medial OFC, an area implicated in reward behaviour. Seifritz, *Biol. Psychiatry*, 2003, 54, 1367-75 investigated the neural responses of parents to the laughing and crying of unfamiliar infants, and found amygadalar activation in parents responding to crying.

Thus, overall, this body of this literature points to the proper functioning of the OFC as being crucial in the healthy maternal response.

In addition, two studies have specifically examined the fMRI response of the PPD mother to various stimuli. In a first study, Silverman examined the fMRI response to negative words of mothers suffering from PPD, and reported hypometabolsim in both the posterior medial OFC and the amygdala of the PPD mother. Of note, Silverman's FIG. 1 also reports hypometabolism in a large portion of a lateral region of the OFC as well ("S" in FIG. 33 herein). However, Silverman does not recognize the hypometabolism of the lateral OFC region. In a second study, Fahim, *Bipolar Disorders* 2007 9, 541-545, examined the fMRI response of a postpartum psychotic (PPP) mother during passive viewing of emotional film excerpts and compared her fMRI response to that of her healthy twin. Fahim found that a small region in the lateral OFC was hypometabolic in the PPP twin. Of note, Fahim reported that this small OFC region was the only region having a different metabolism.

In addition, King, *NeuroImage,* 30, 2006, 1069-76, investigated the neural correlates of appropriate violent and compassionate behaviours, and reports that the same circuit involving the amygdala and ventromedial prefrontal cortex was activated when participants acted in a context-appropriate manner. King concluded that this circuit was strongly activated when humans were engaged in "doing the right thing."

Figure 33:
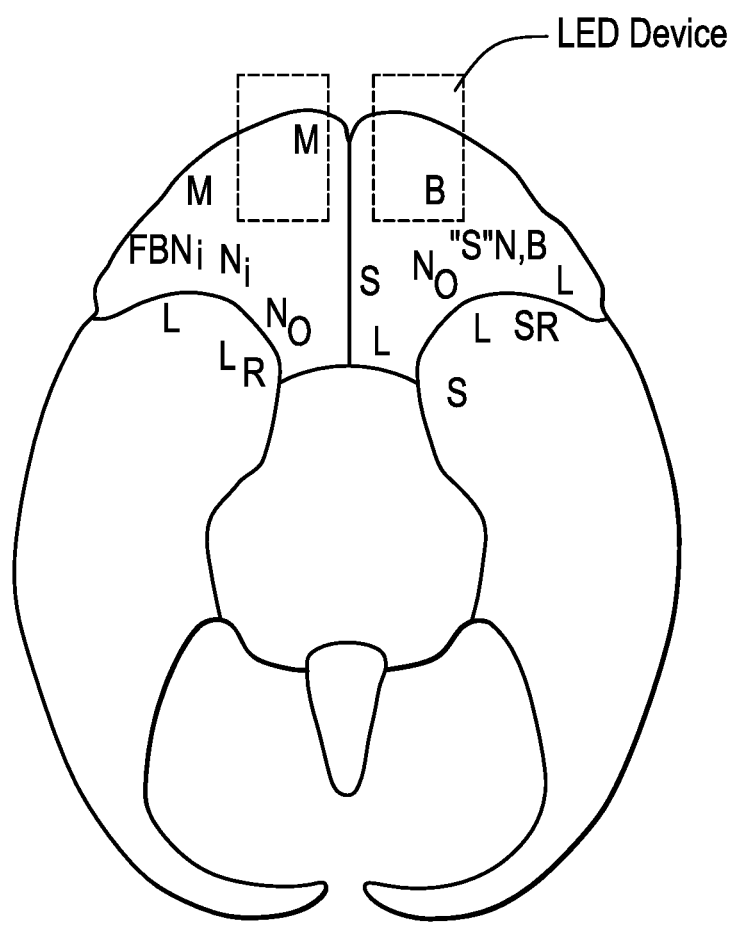
FIG. 33 is a bottom view of the human brain showing the proximity of the mother zone MZ to the inserted device.

FIG. 33 discloses a bottom view of the brain in which the capitals letter designations (such as M and L) identify regions of the orbitofrontal cortex or temporal lobe implicated by the various authors discussed above. For example, the capital letter S in FIG. 33 designates the regions of the orbitofrontal cortex and temporal lobe identified as important by Silverman above.

Therefore, when all of these studies are rationalized, it appears that there exists a fairly contiguous region of gray matter running medially and posteriorly from the lateral OFC through the temporal pole and to the amygdala that appears to play an important role mediating healthy responses of a mother towards her child. See FIG. 33. For the purposes of the present invention, this region will be called the Maternal Zone (MZ). In short, it appears that the MZ is activated when the healthy mother is engaged in socially desirable activity towards her child. Moreover, the literature (Silverman and Fahim) appears to report that the MZ is somewhat hypometabolic is PPD and PPP mothers.

Moreover, further examination of FIG. 33 reveals that there appears to be a cluster of data five points (Fahim, Bartles, Nitschke, Minagawa-Kawai and Silverman) situated in the anterior portion of the lateral orbitofrontal cortex. This cluster is of note for a number of reasons. First, the multiplicity of researchers who found statistically significant differences in maternal fMRIs at this site over a range of test conditions indicates that this site may be a lynchpin in the maternal emotional framework. Second, this site appears to be the only one in which researchers found not only the expression of joy in mothers viewing their own babies (Nitschke and Minagawa-Kawai) but also an attenuated response to stimuli in PPD mothers (Silverman and Fahim). Lastly, Moses-Kolko, *Fertil. Steril.,* 2008 March 89(3) 685-92 has reported that the left and right lateral OFC were two of the few sites in the PPD brain to display decreased serotonin receptor binding. Of note, the Moses-Kolko paper appears to lend credence to Fahim's hypothesis that the cause of PPD was related to the estrogen-driven decrease in the serotonergic system in the OFC. Therefore, because the site of this cluster appears to evoke baby-related joy in mothers, have attenuated activity in PPD mothers, and have decreased biochemical activity pertinent to emotion in PPD mothers, this site is a prime candidate for the treatments of the present invention.

In addition, Roelofs, *SCAN* (2009) 4, 50-58 reports that the left lateral OFC (BA47/12) is implicated in the neural control of social emotional behavior and has a general role in overriding dominant-stimulus-response mappings in favor of rule-driven associations. Roelofs also predicts that disturbances such as social avoidance tendencies involved altered responses of the left lateral orbitofrontal cortex. Therefore, it is possible that improving the activation of the left lateral OFC could improve deficits in the mother-child interaction stemming from such a disturbance.

Therefore, in light of the above studies, and without wishing to be tied to a theory, it is believed that the hypometabolism of MZ plays a predominant and direct role in the depressed state of the PPD mother.

It is further believed that the hypometabolism of the MZ can be reversed by low level laser therapy ("LLLT") treatment of the MZ with red/near infrared light ("red/NIR light"). In particular, it is believed that red/NIR light will beneficially act upon the MZ through the following avenues:

e) increasing the amount of ATP in the MZ;
f) increasing the amount of BDNF in the MZ;
g) increasing the amount of bcl-2 in the MZ, and
h) increasing the amount of sprouting in the MZ Also shown in FIG. 33 is a dashed outline of the approximate location of the LED-laden tube of the present devices. As seen, eye-socket based LEDs appear to be particularly well placed for delivery of NIR/red light to the Mother Zone.
(ACA)

Figure 34:
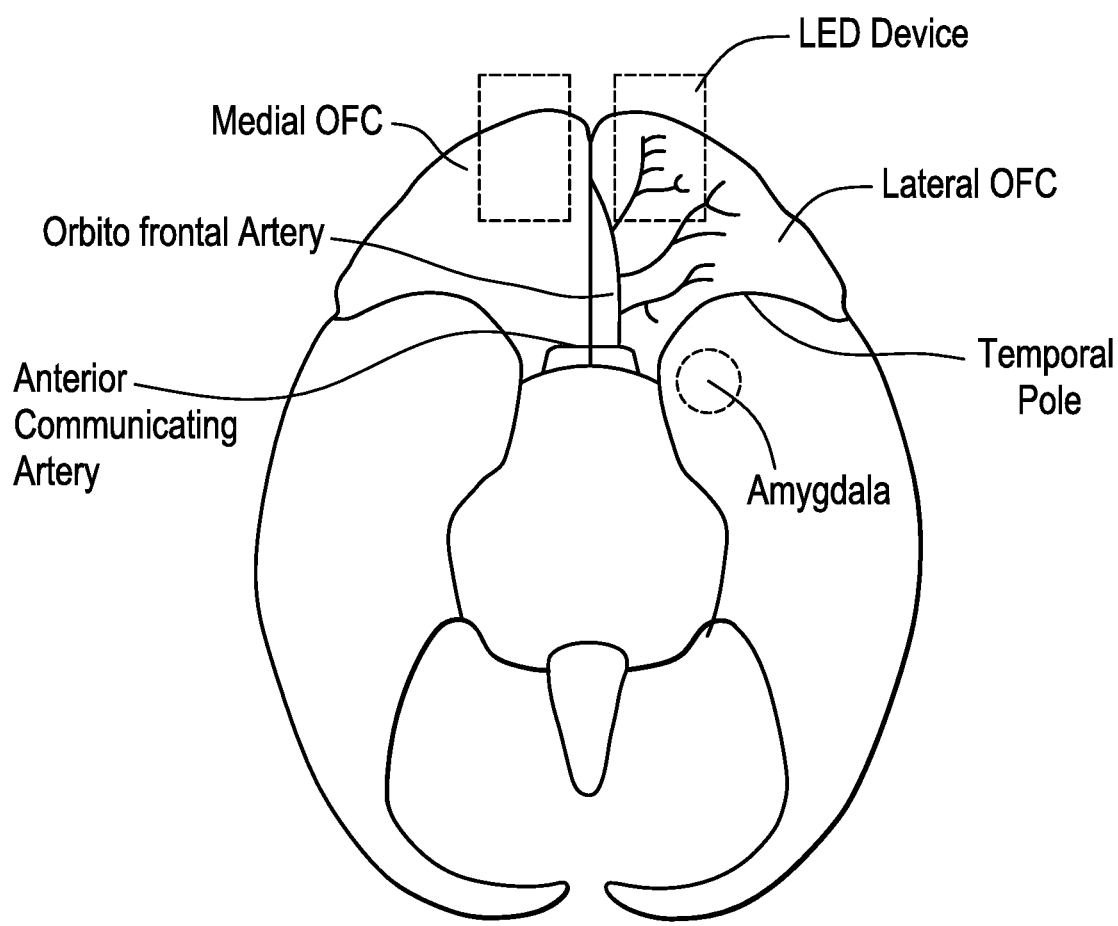
FIG. 34 is a bottom view of the human brain showing the proximity of the anterior communicating artery to the inserted device.

A great percentage of aneurysms arise from the anterior communicating artery of the Circle of Willis. About 30,000 people each year in the US suffer a rupture of an aneurysm of the cerebral vasculature. About 85% of sac-based aneurysms arise from the arteries of the Circle of Willis, with the anterior communicating artery being the most prevalent (35%). Keedy, *McGill Journal of Medicine,* 2006, 9(2), 141-146. As shown in FIG. 34, there is a dashed outline of the approximate location of the LED-laden tube of the present devices adapted to treat conditions arising from the anterior communicating artery or orbitofrontal artery. As seen, eye socket based LEDs appear to be particularly well placed for delivery of NIR/red light to the regions surrounding anterior communicating artery or orbitofrontal artery.
(Behaviours)

It is proposed to pair use of infrared nasal clips with daily routines in order to maximize adherence to the regimen. One advantage we seek is to make a device that is:

Less disruptive
Less invasive
Less discomforting
Shorter duration

In addition, simultaneous use of red light therapy with established behavior change interventions such as meditation, exposure therapy, cognitive behavioral therapy, and guided imagery can enhance the efficacy of those treatments.

A related approach for enhancing adherence purely for the stimulation of the OFC is to use the Premack Principle. The Premack Principle states: If behavior B is of higher probability than behavior A, then behavior A can be made more probable by making behavior B contingent upon it. This is also known as "relativity theory of reinforcement", based on the work of David Premack. As one example, if a person routinely drinks a cup of coffee, we would make that behavior incumbent on first using the red light therapy. Behaviors can also be simultaneously paired together in some cases e.g., use nasal clip while reading the morning paper. If you don't have the clip in, you don't get to read the paper.

It is contemplated to use red light in conjunction with exposure therapy for fears, phobias and traumas. There are three ways to expose clients to their fears during systematic desensitization. First, exposure to fears can be accomplished through mental imagery. This approach can be more convenient and allows patients to complete treatment without ever leaving their therapist's office. Second, in vivo (direct exposure to the feared stimulus) is also possible. This option can be more complex (e.g., going to a dental office to provide exposure for a patient with a dental phobia), but appears to produce outcomes superior to imaginal exposure. Third, computer simulation (virtual reality) has been successfully used as a means of exposing a patient to feared stimuli. Simultaneous use of red light during these exposures might enhance the efficacy/benefit of the treatment.

Professional use of these devices could include:

a) 1st Responders EMS—This could be part of every head injury assessment and treatment could begin immediately while the patient is being transported to the trauma center;
b) Military Battlefield—Much like the role of the EMS, first responders, this could be part of a field medic, special forces units, MASH units, and larger base hospitals, and
c) Sports Trainers, Coaches—Administration could begin immediately on the field after players sustain a concussion. This could be therapeutic and preventative for Chronic Traumatic Encephalopathy.

Consumer and self-administered uses of these devices could include:

d) Post-Partum Depression—Newly discharged mothers would use this in the peri-partum period, provided it was attractively packaged and marketed;
e) Alzheimer's Disease Benign Senile Forgetfulness—Senior citizens could administer treatments themselves or have in home care givers provide assistance for therapy. Venues would include assisted living and skilled nursing facilities;
f) Post Concussive Syndrome—Children and adolescents would benefit from therapy as many struggle with executive function tasks (math and reading) as they recover from sports related concussions. This has vast society implications;
g) First Aid Kits—Devices could be part of every First Aid kit for car, traveling, camping, home use, etc;
h) Acute Sports Injury|Concussion—Apart from the physical "contact" sports such as football, there potentially is a role for all sports including hiking, diving, particularly outdoorsman that are remote and not near medical care.

We claim:

1. A method comprising:
   a) placing a light-emitting portion of a device comprising a near infrared LED against an eyelid of a patient having a brain disorder in a location between an upper portion of an eye and a corresponding eye socket of the patient,
   b) moving the device posteriorly so that at least a portion thereof sits within a portion of an outer region of the eye socket, and
   c) actuating the LED to deliver near infrared light to an orbitofrontal cortex of the patient.

2. The method of claim 1 wherein the light is emitted on a side of the device opposing the eye.

3. The method of claim 1 wherein the light-emitting portion comprises a proximal near infrared LED and a distal light transmitting portion.

4. The method of claim 1 wherein the device has a distal end portion that is substantially concavo-convex.

5. The method of claim 1 wherein the device further comprises electronics adapted to provide a substantially constant current.

6. The method of claim 1 wherein the device is carried on a mask.

7. The method of claim 1 wherein the LED is carried on a hinge.

* * * * *